United States Patent
Ma et al.

(10) Patent No.: US 9,404,105 B2
(45) Date of Patent: Aug. 2, 2016

(54) POLYHEDRAL CAGE-CONTAINING MESOPOROUS METAL-ORGANIC FRAMEWORKS AS PLATFORM FOR BIOCATALYSIS, METHODS OF MAKING THESE FRAMEWORKS, AND METHODS OF USING THESE FRAMEWORKS

(75) Inventors: Shengqian Ma, Tampa, FL (US); Li-June Ming, Lutz, FL (US); Yao Chen, Tampa, FL (US); Vasiliki Lykourinou, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 201 days.

(21) Appl. No.: 14/124,849

(22) PCT Filed: Jun. 15, 2012

(86) PCT No.: PCT/US2012/042708
§ 371 (c)(1),
(2), (4) Date: Dec. 9, 2013

(87) PCT Pub. No.: WO2012/174402
PCT Pub. Date: Dec. 20, 2012

(65) Prior Publication Data
US 2015/0087044 A1 Mar. 26, 2015

Related U.S. Application Data

(60) Provisional application No. 61/497,806, filed on Jun. 16, 2011.

(51) Int. Cl.
*C12N 9/96* (2006.01)
*C12N 9/08* (2006.01)
*C12N 11/14* (2006.01)

(52) U.S. Cl.
CPC ............... *C12N 9/96* (2013.01); *C12N 9/0065* (2013.01); *C12N 11/14* (2013.01)

(58) Field of Classification Search
None
See application file for complete search history.

(56) References Cited

U.S. PATENT DOCUMENTS

2008/0188677 A1 8/2008 Schubert
2011/0104213 A1 5/2011 Rosi

OTHER PUBLICATIONS

Tanabe and Cohen, "Postsynthetic modfication of metal-organic frameworks—a progress report", Chem. Soc. Rev. 40: 498-519 (2011).*
Park, Young Kwan, et al., "Crystal structure and guest uptake of a mesoporous metal-organic framework containing cages of 3.9 and 4.7 nm in diameter", Angewandte Chemie International Edition, Aug. 7, 2007, vol. 46, No. 43, pp. 8230-8233.
Pisklak, Thomas J. et al., "Hybrid materials for immobilization of MP-11 catalyst", Topics in catalysis, Aug. 2006, vol. 38, No. 4, pp. 269-278.
Fang, Qian-Rong, et al., "Functional mesoporous metal-organic frameworks for the capture of heavy metal ions and size-selective catalysis," Inorganic chemistry, Nov. 17, 2010, vol. 48, No. 24, pp. 11637-11642.
Lykourinou, Vasiliki, et al., "Immobilization of MP-11 into a mesoporous metal-organic framework, MP-11@mesoMOF: a new platform for enzymatic catalysis", Journal of the American Chemical Society, Jun. 17, 2011, vol. 133, No. 27, pp. 10382-10385.
Bommarius, e. a. (Jun. 27, 2013). Stabilizing biocatalysts. Chemical Society Reviews, 42(15), 6534-6565.
Chen, et al. (Aug. 3, 2012). How Can Proteins Enter the Interior of a MOF? Investigation of Cytochrome c Translocation into a MOF Consisting of Mesoporous Cages with Microporous Windows. Journal of the American Chemical Society, 134(32), 13188-13191.
Chen, Y., Tran, H., & Shengqian, M. (Nov. 20, 2012). Biomimetic Catalysis of a Porous Iron-Based Metal—Metalloporphyrin Framework. Inorganic Chemistry, 51(23), 12600-12602.
Deng, et al. (May 25, 2012). Large-Pore Apertures in a Series of Metal-Organic Frameworks. Science , 336(6084), 1018-1023.
Hanefeld, U., Cao, L., & Magner, E. (Jun. 27, 2013). Enzyme immobilisation: fundamentals and application. Chemical Society Reviews, 42(15), 6211-6212.
Hartmann, M., & Kostrov, X. (Jun. 13, 2013). Immobilization of enzymes on porous silicas—benefits and challenges. Chemical Society Reviews, 42(15), 6277-6289.
Hudlicky, T. (Jun. 15, 2011). Introduction to Enzymes in Synthesis. Chemical reviews, 111(7), 3995-3997.
Lee, C. H., Lin, T. S., & Mou, C. Y. (Feb. 23, 2009). Mesoporous materials for encapsulating enzymes. Nano Today, 4(2), 165-179.
Lykourinou, V., Chen, Y., Wang, X. S., Meng, L., Hoang, T., Ming, L. J., . . . & Ma, S. (Jun. 17, 2011). Immobilization of MP-11 into a mesoporous metal—organic framework, MP-11@ mesoMOF: a new platform for enzymatic catalysis. Journal of the American Chemical Society, 133(27), 10382-10385.
Zhou, Z., & Hartmann, M. (Apr. 8, 2013). Progress in enzyme immobilization in ordered mesoporous materials and related applications. Chemical Society Reviews, 42(9), 3894-3912.
Pisklak, T. J., Macias, M., Coutinho, D. H., Huang, R. S., & Balkus Jr, K. J. (Aug. 2006). Hybrid materials for immobilization of MP-11 catalyst. Topics in catalysis, 38(4), 269-278.
Tran, D. N., & Balkus Jr, K. J. (Jun. 5, 2011). Perspective of recent progress in immobilization of enzymes. ACS Catalysis, 1(8), 956-968.
Zhou, Z., & Hartmann, M. (Oct. 11, 2012). Recent Progress in Biocatalysis with Enzymes Immobilized on Mesoporous Hosts. Topics in Catalysis, 55(16-18), 1081-1100.
An, et al., "Organic-Inorganic Hybrids with Three-Dimensional Supramolecular Channels Based on Anderson Type Polyoxoanions", Journal of Molecular Structure, vol. 743, No. 1-3, May 31, 2005.
Janiak, et al., "MOFs, MILs and More: Concepts, Properties and Applications for Porous Coordination Networks (PCNs)", New Journal of Chemistry, vol. 34, No. 11., Jan. 1, 2010.
Foreign Search Results for EP 12800538, dated Oct. 13, 2014.

* cited by examiner

*Primary Examiner* — Anand Desai
(74) *Attorney, Agent, or Firm* — Thomas Horstemeyer, LLP

(57) ABSTRACT

Embodiments of the present disclosure provide compositions including polyhedral mesoporous metal-organic framework including a biomolecule (e.g., enzyme), methods of making these compositions, methods of use, and the like.

14 Claims, 20 Drawing Sheets

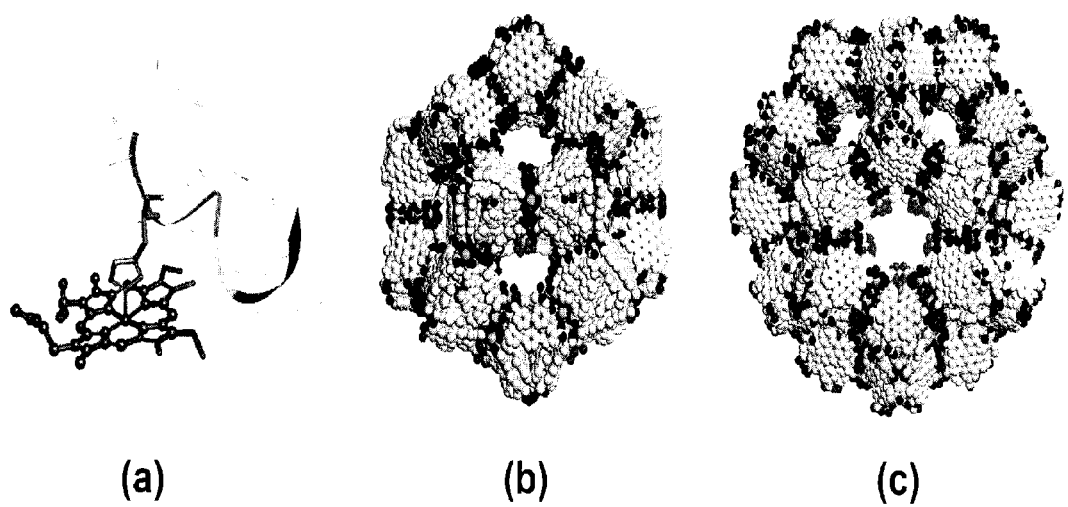
FIG. 1.1

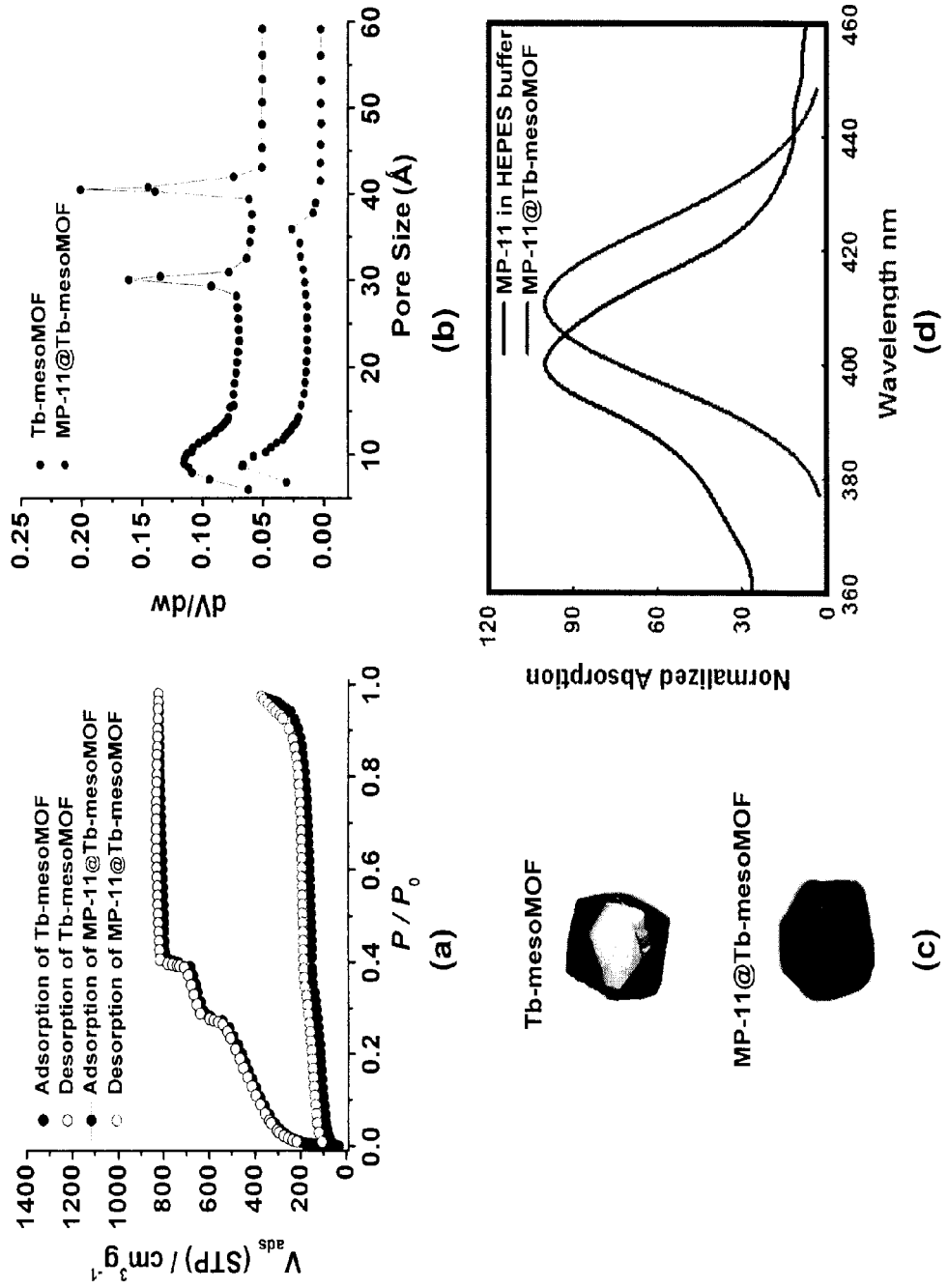
FIG. 1.2

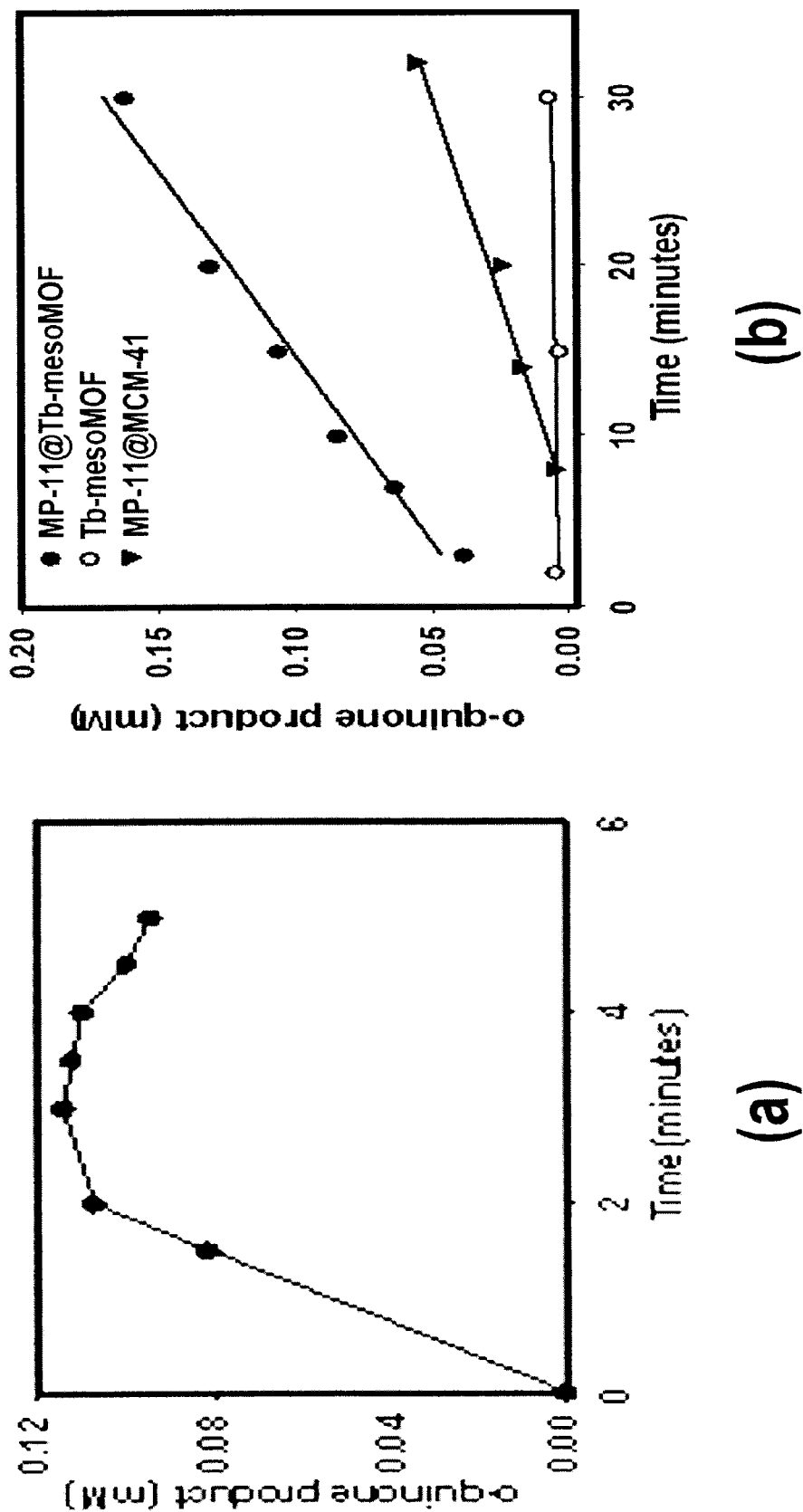
FIG. 1.3

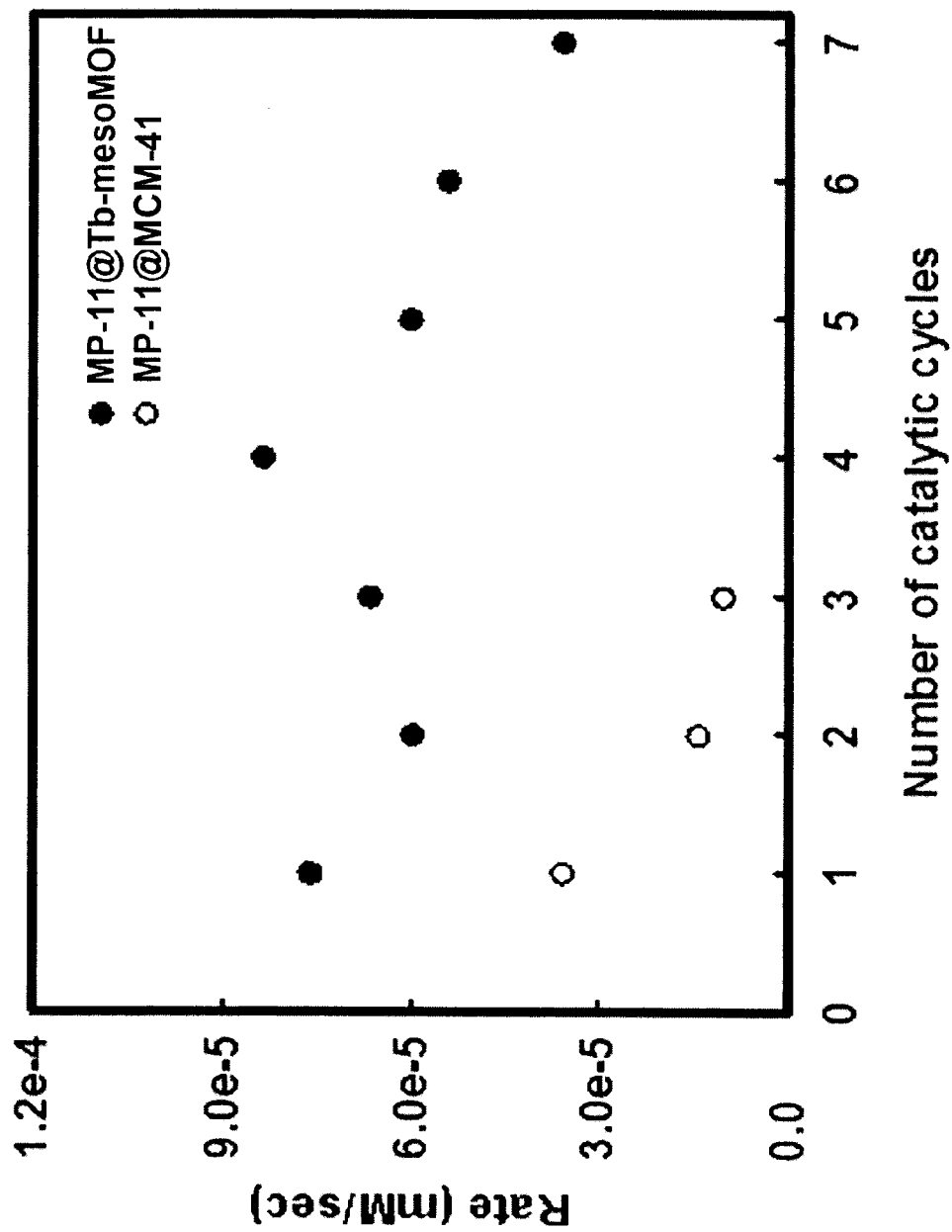
FIG. 1.4

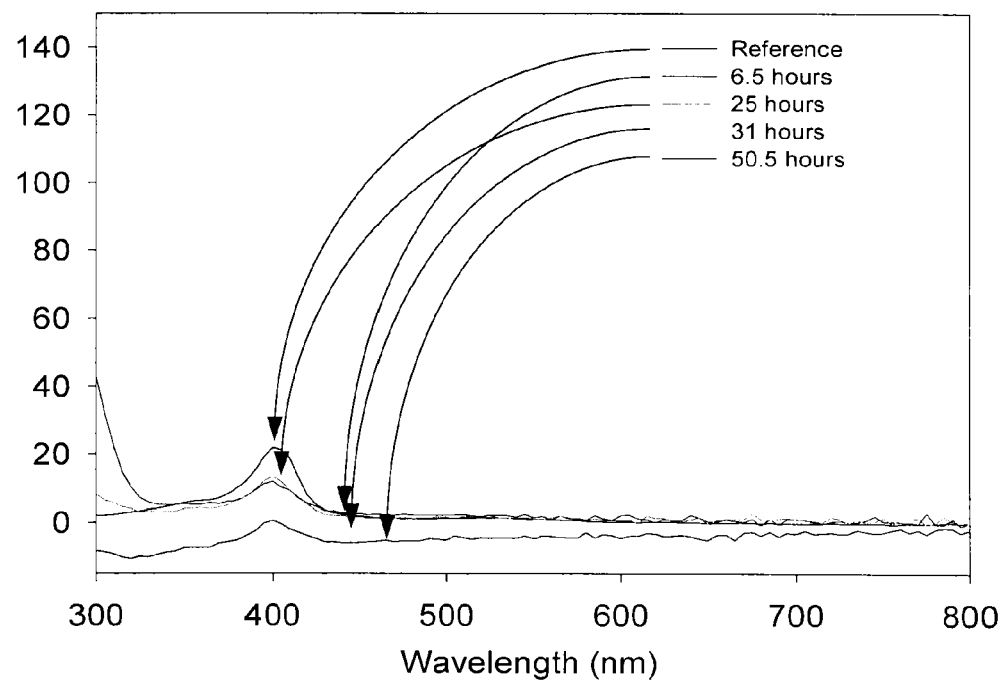
FIG. 1.5
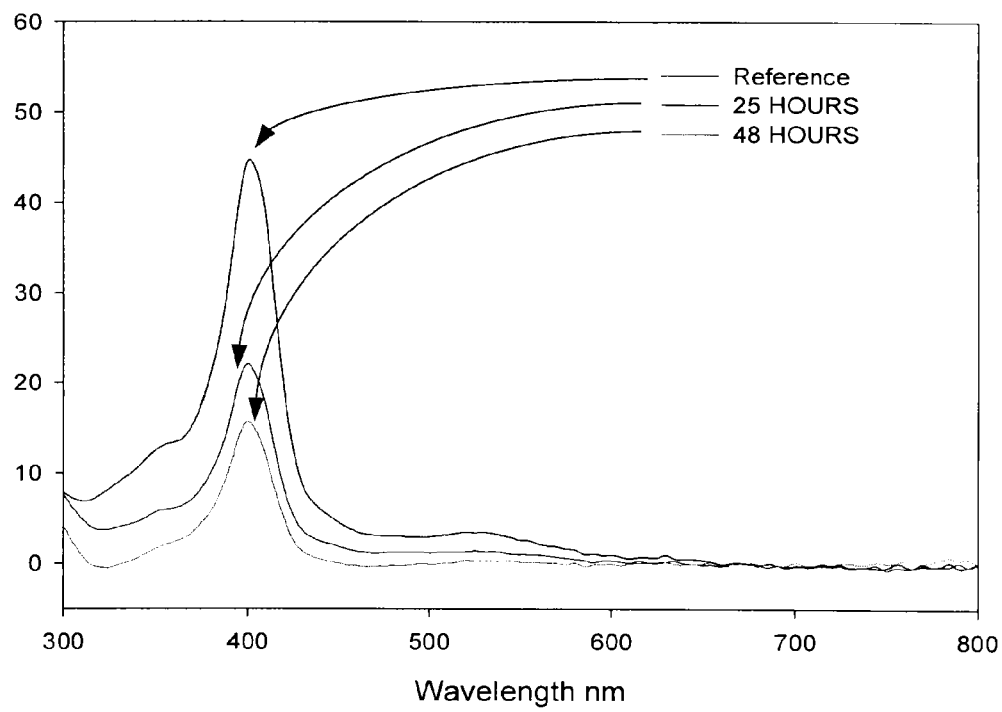
FIG. 1.6

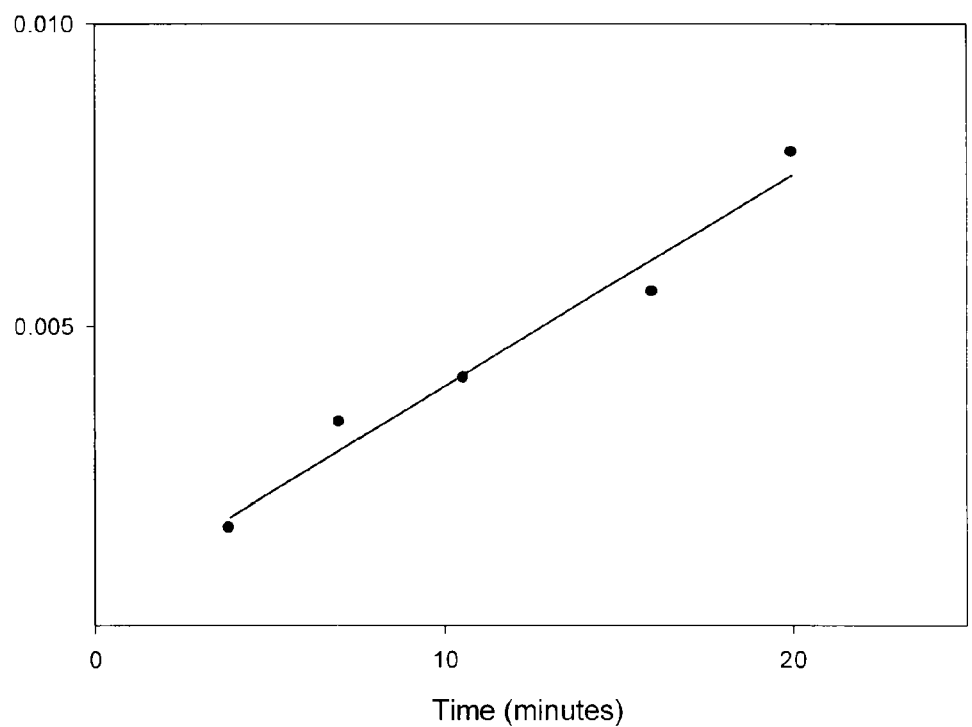
FIG. 1.7
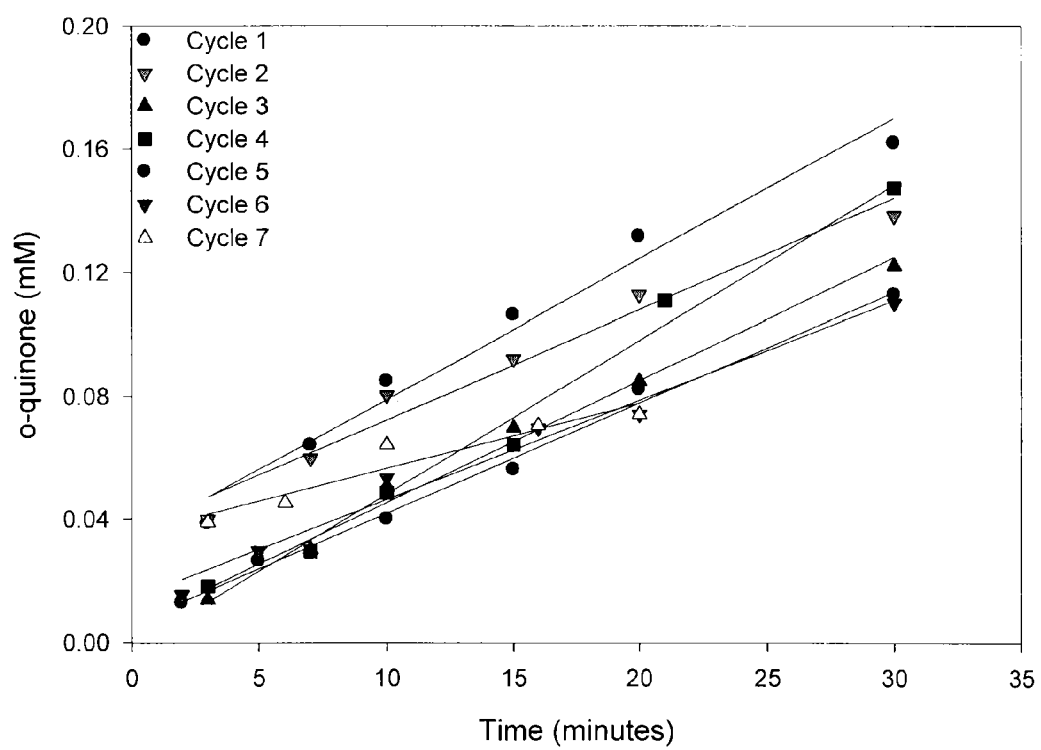
FIG. 1.8

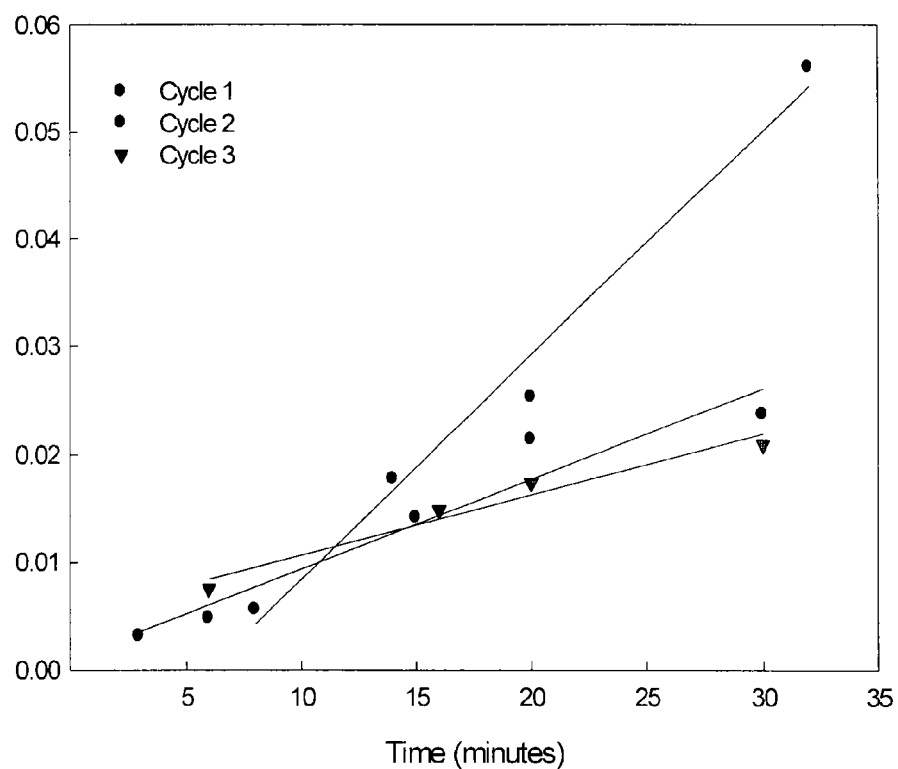
FIG. 1.9
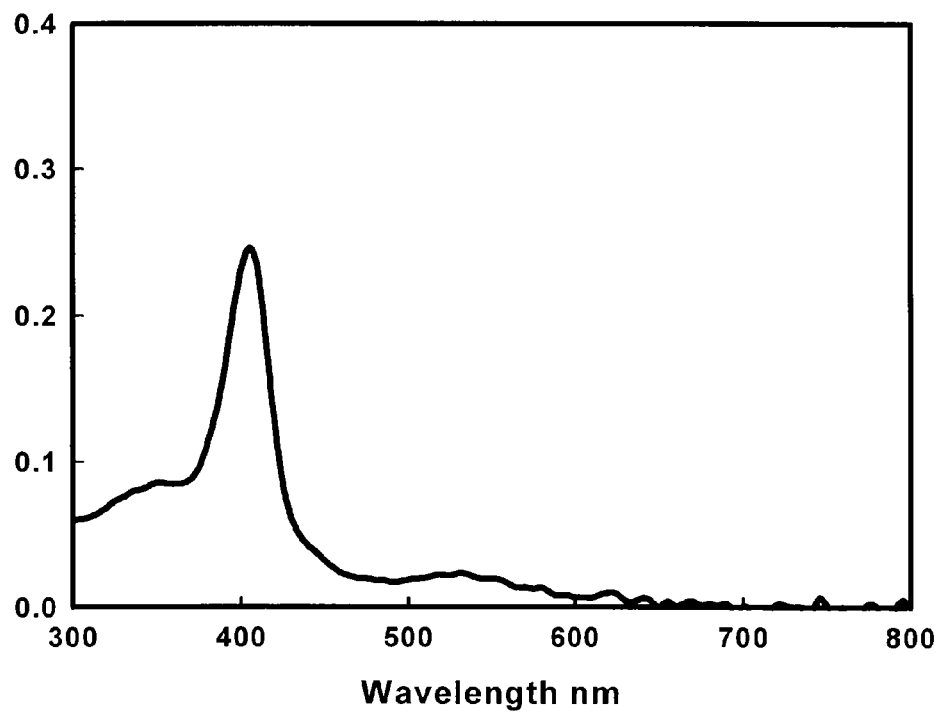
FIG. 1.10

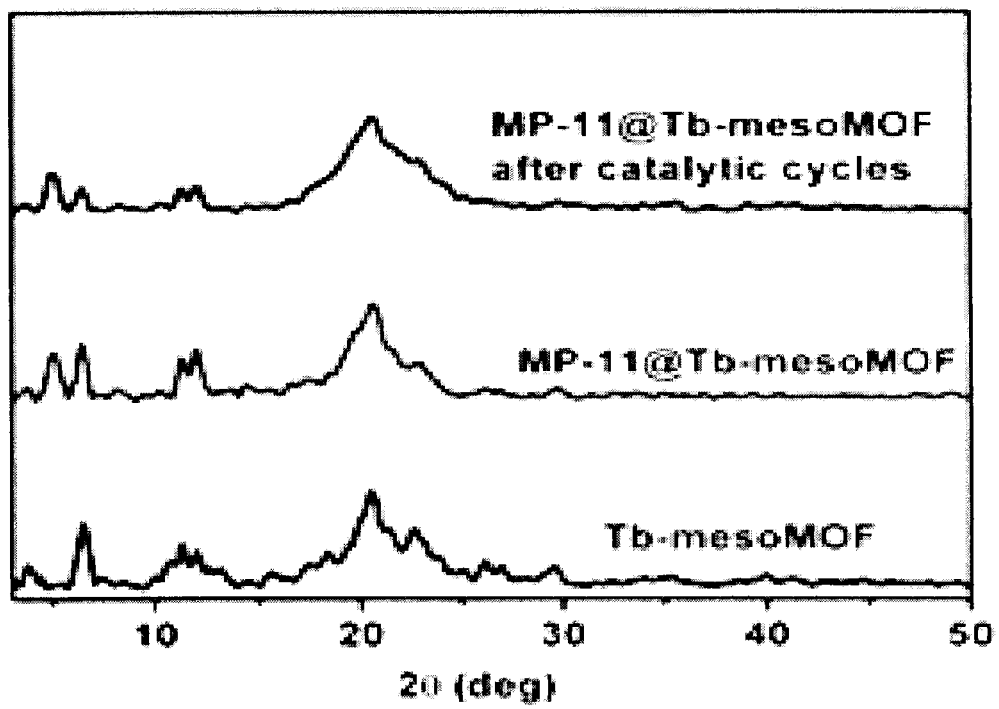
FIG. 1.11
Table S1. Summary of reaction rates at different catalytic cycles.
|  | Rate of MP-11@MCM-41 (mM/sec) | Rate of MP-11@Tb-mesoMOF (mM/sec) |
| --- | --- | --- |
| Cycle 1 | $3.57 \times 10^{-5}$ | $7.58 \times 10^{-5}$ |
| Cycle 2 | $1.40 \times 10^{-5}$ | $5.97 \times 10^{-5}$ |
| Cycle 3 | $1.00 \times 10^{-5}$ | $6.64 \times 10^{-5}$ |
| Cycle 4 |  | $8.34 \times 10^{-5}$ |
| Cycle 5 |  | $6.00 \times 10^{-5}$ |
| Cycle 6 |  | $5.40 \times 10^{-5}$ |
| Cycle 7 |  | $3.56 \times 10^{-5}$ |
FIG. 1.12

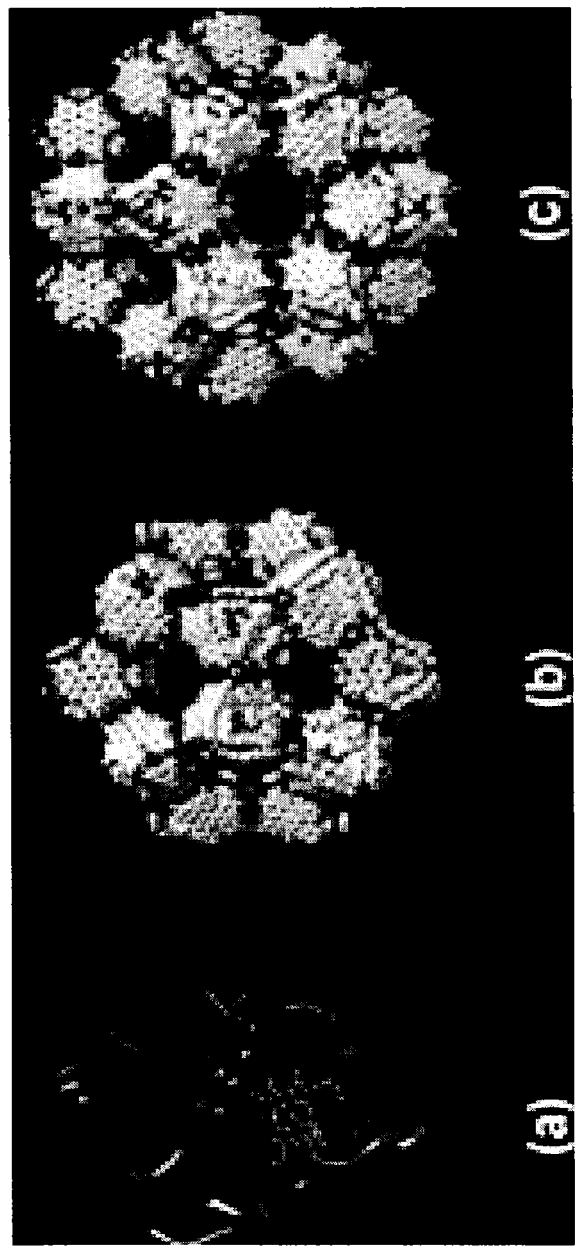
FIG. 2.1

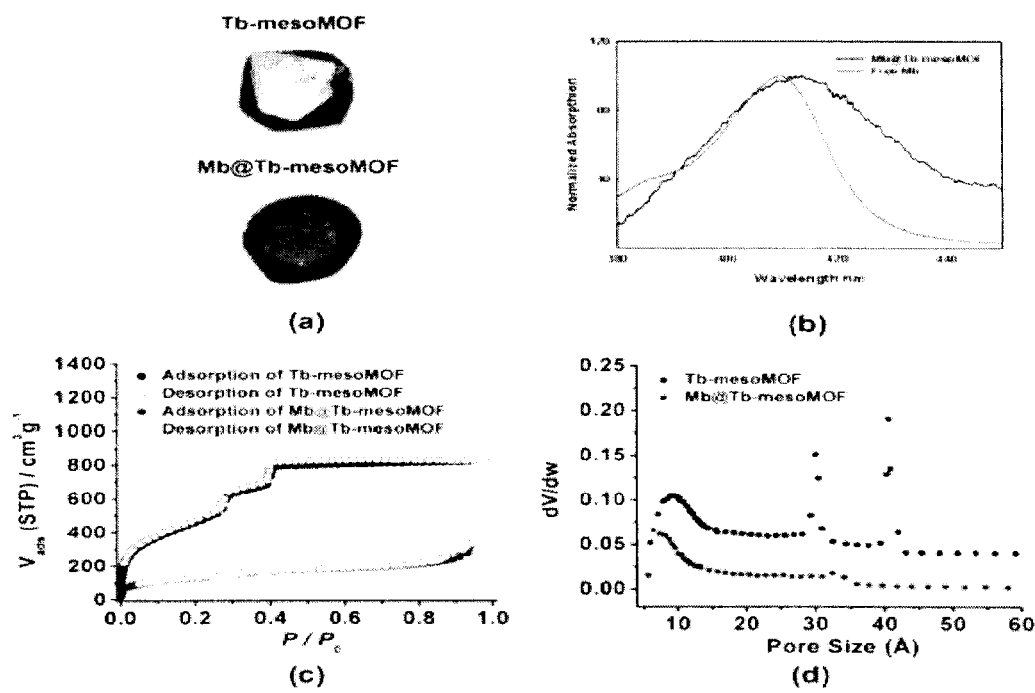
FIG. 2.2

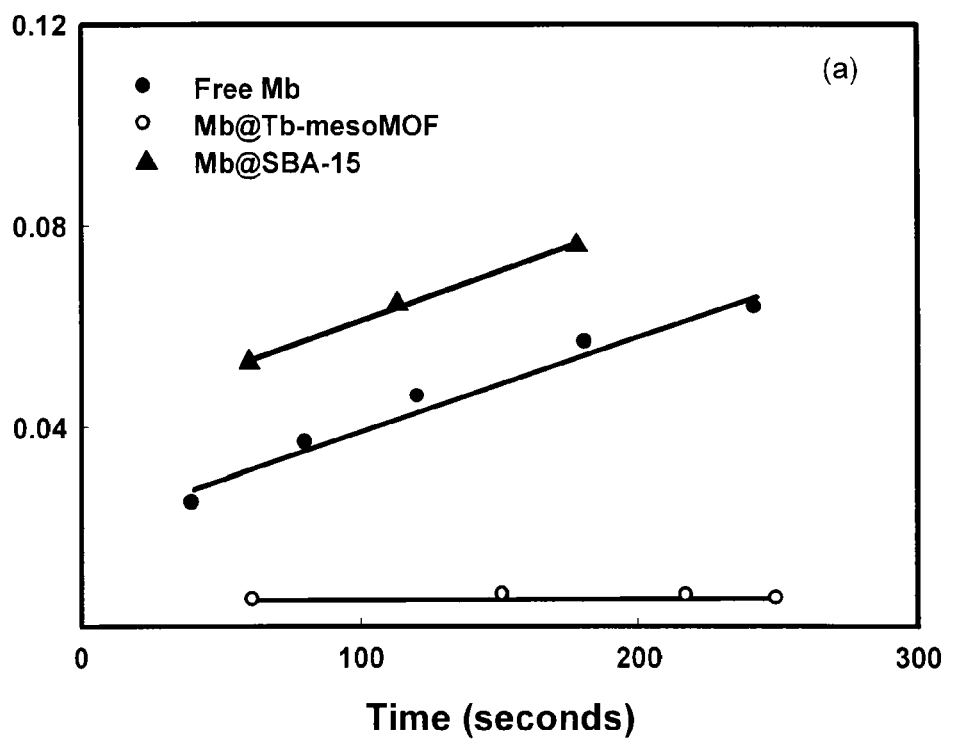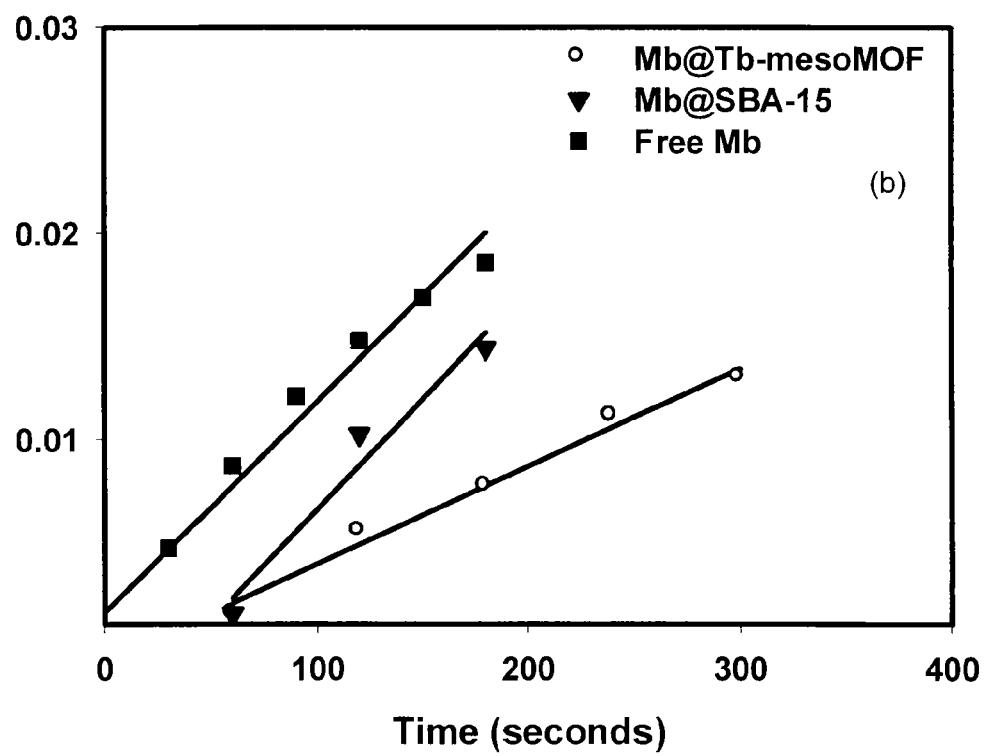
FIG. 2.3

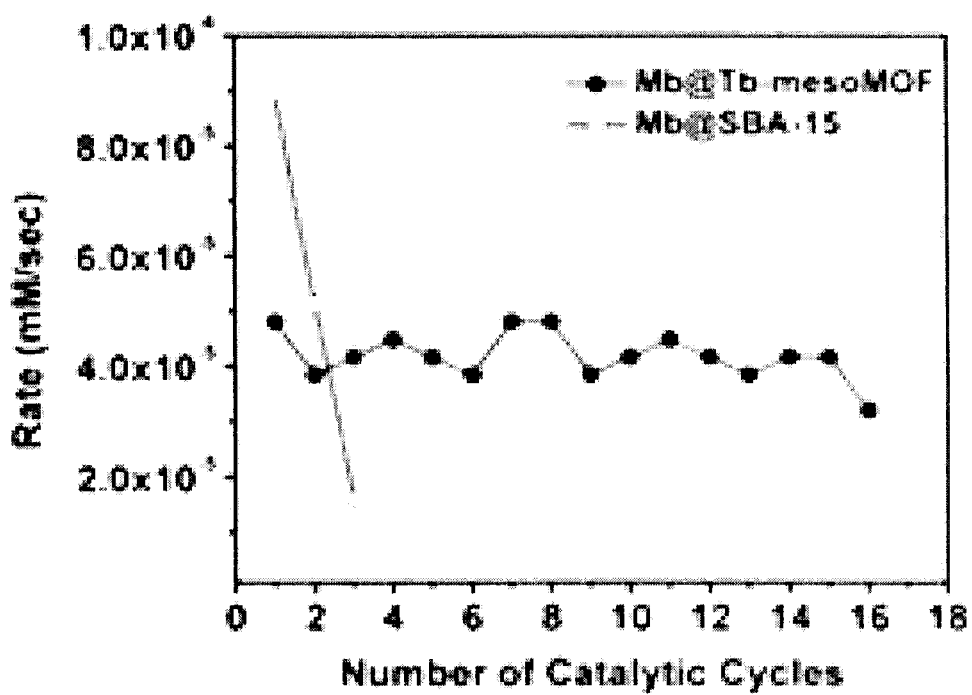
FIG. 2.4
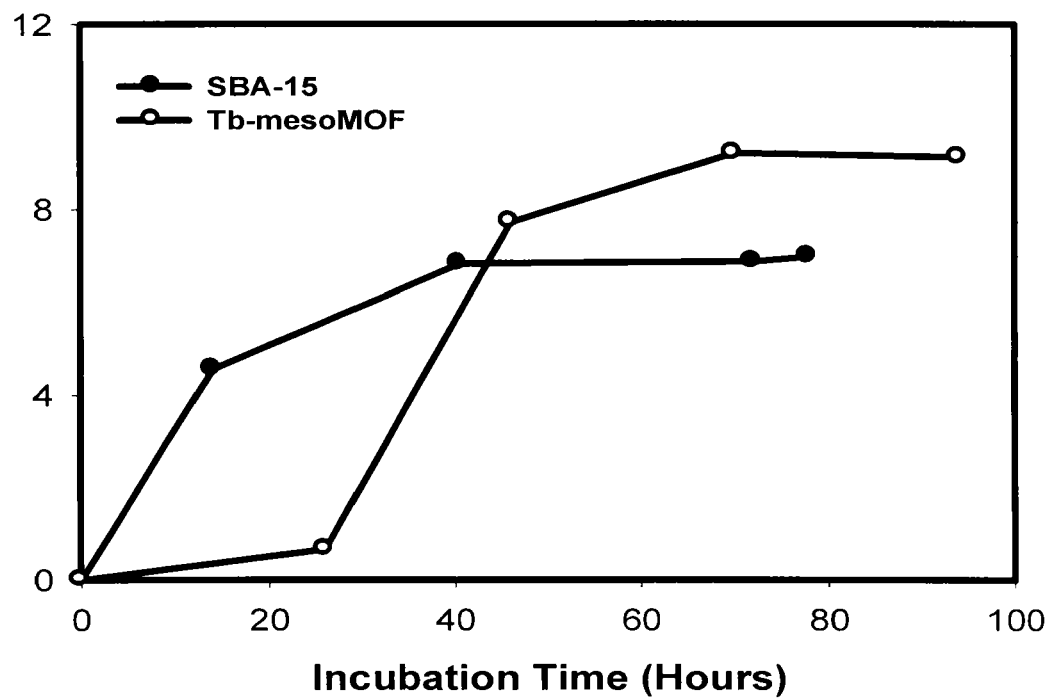
FIG. 2.5

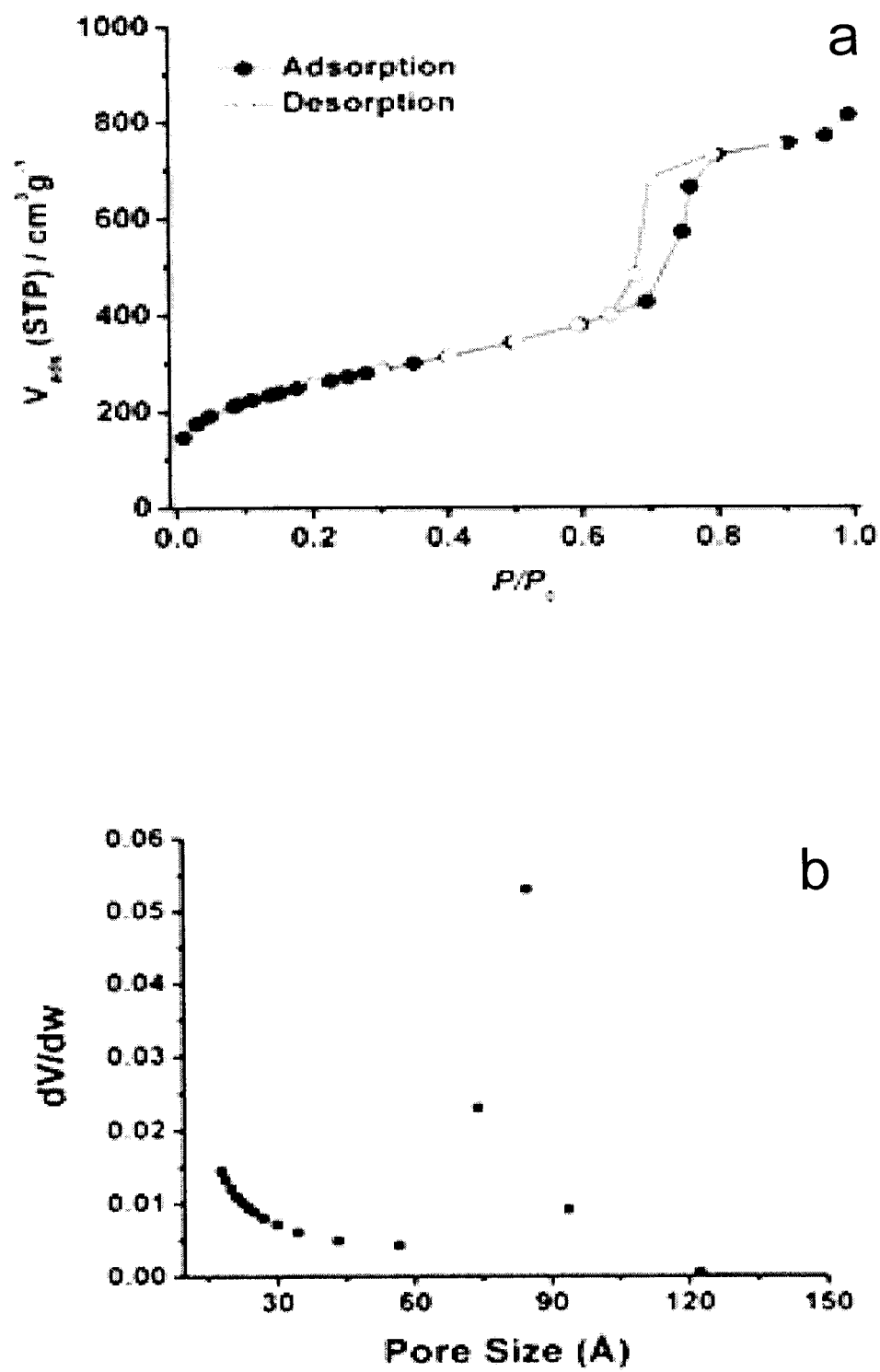
FIG. 2.6

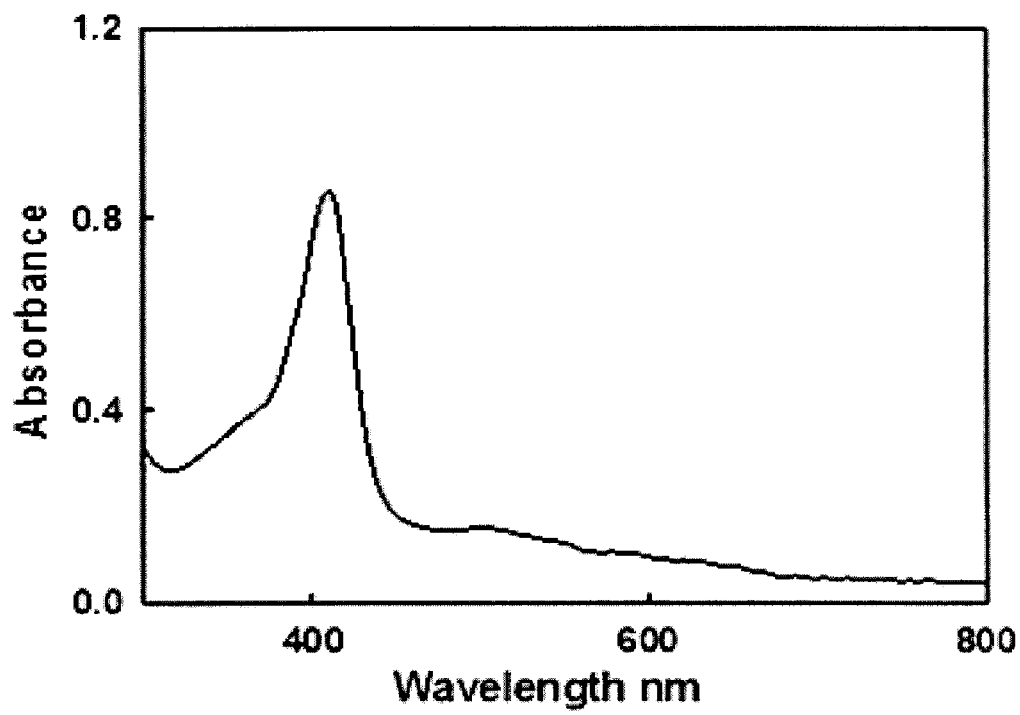
FIG. 2.7
*Table S1.* Summary of reaction rates at different catalytic cycles.
| Cycle | Mb@TbmesoMOF (mM/sec) | Mb@ SBA-15 (mM/sec) |
|---|---|---|
| 1 | $4.80 \times 10^{-5}$ | $8.96 \times 10^{-5}$ |
| 2 | $3.84 \times 10^{-5}$ | $5.12 \times 10^{-5}$ |
| 3 | $4.16 \times 10^{-5}$ | $1.60 \times 10^{-5}$ |
| 4 | $4.48 \times 10^{-5}$ | |
| 5 | $4.16 \times 10^{-5}$ | |
| 6 | $3.84 \times 10^{-5}$ | |
| 7 | $4.80 \times 10^{-5}$ | |
| 8 | $4.80 \times 10^{-5}$ | |
| 9 | $3.84 \times 10^{-5}$ | |
| 10 | $4.16 \times 10^{-5}$ | |
| 11 | $4.48 \times 10^{-5}$ | |
| 12 | $4.16 \times 10^{-5}$ | |
| 13 | $3.84 \times 10^{-5}$ | |
| 14 | $4.16 \times 10^{-5}$ | |
| 15 | $4.16 \times 10^{-5}$ | |
| 16 | $3.20 \times 10^{-5}$ | |
FIG. 2.8

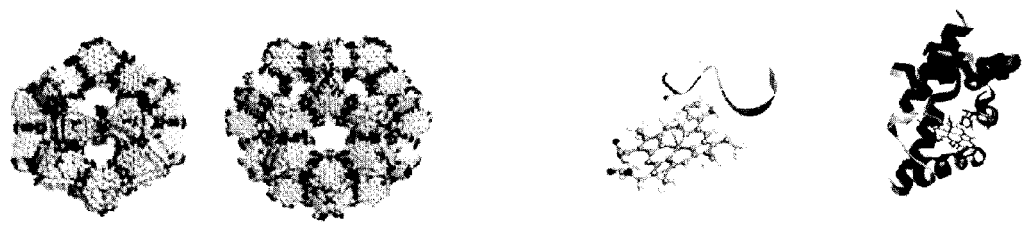
FIG. 3.1A and B
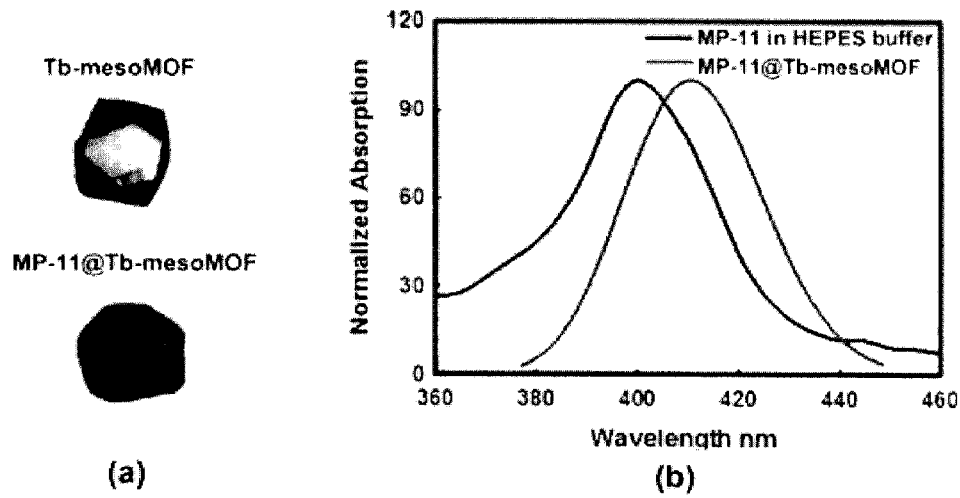
FIG. 3.2A and B

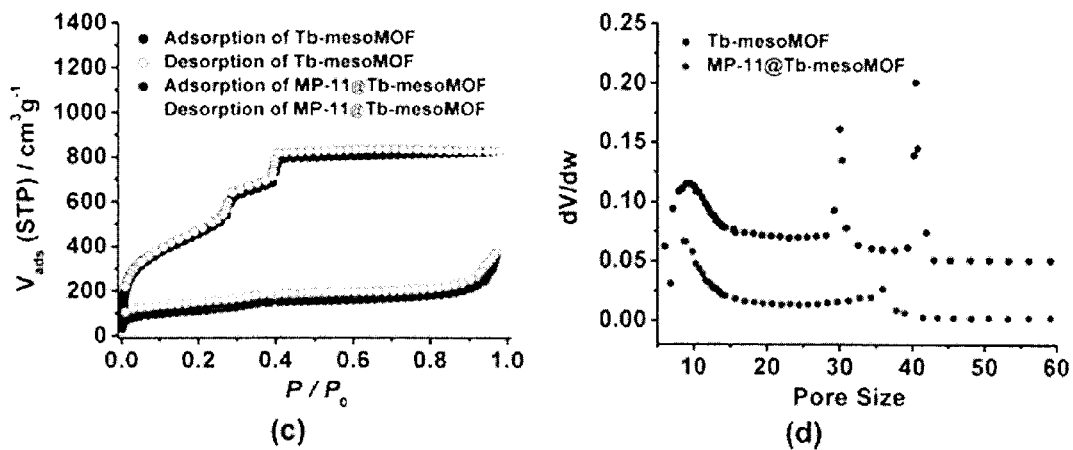
FIG. 3.2C and D
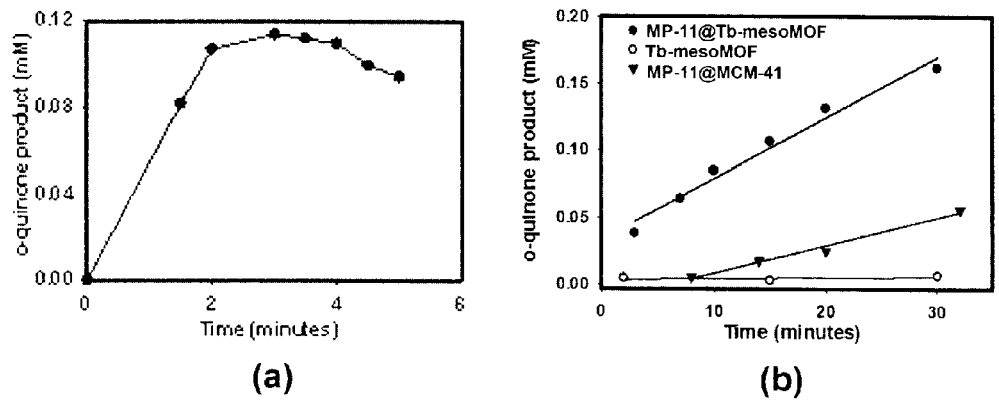
FIG. 3.3

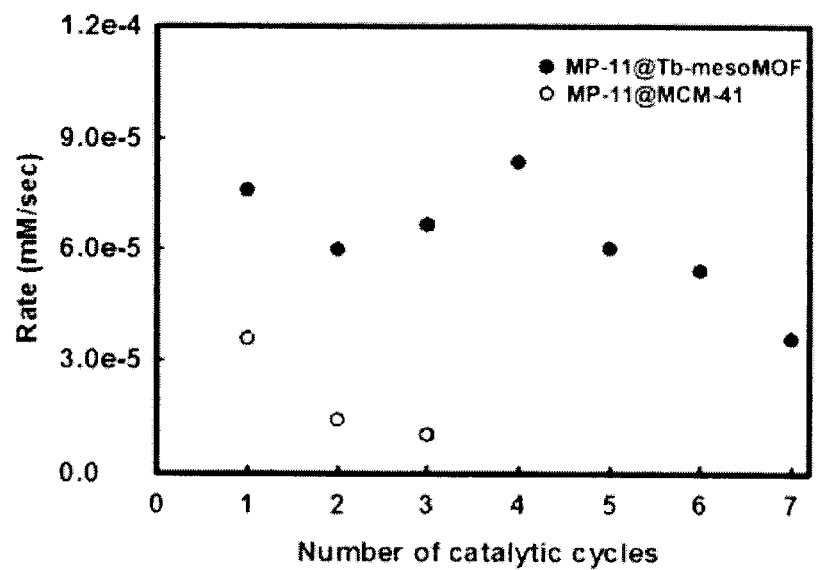
FIG. 3.4

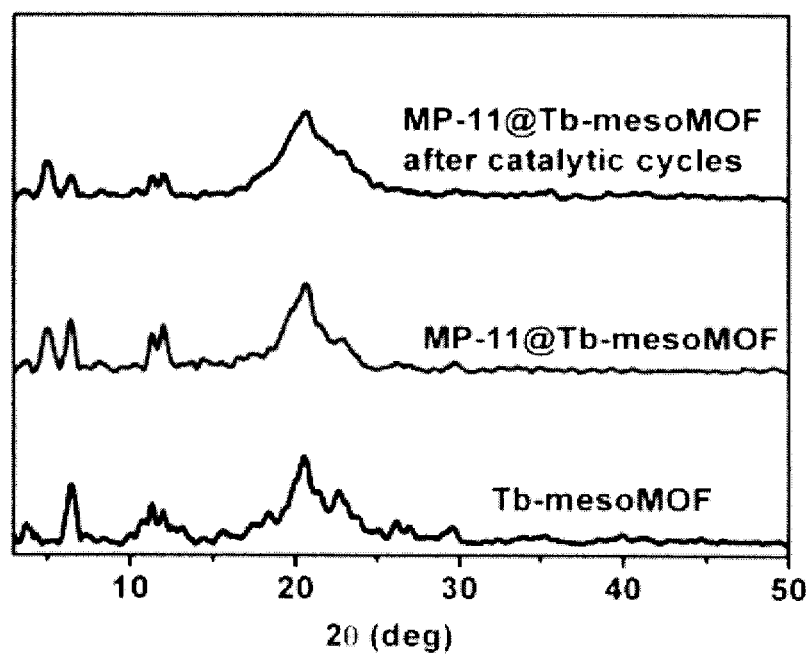
FIG. 3.5

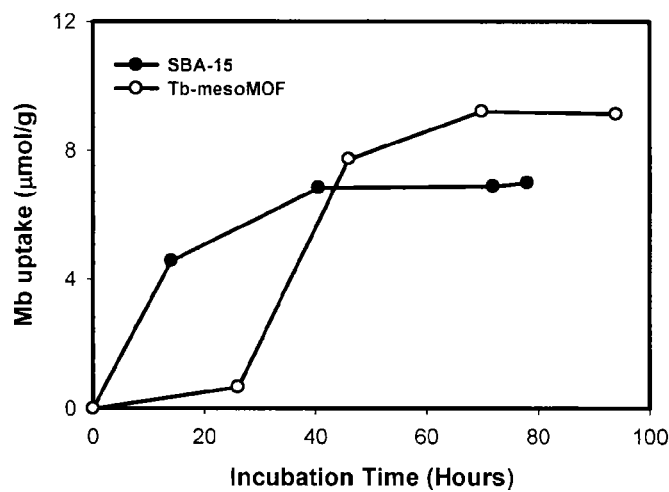
FIG. 3.6
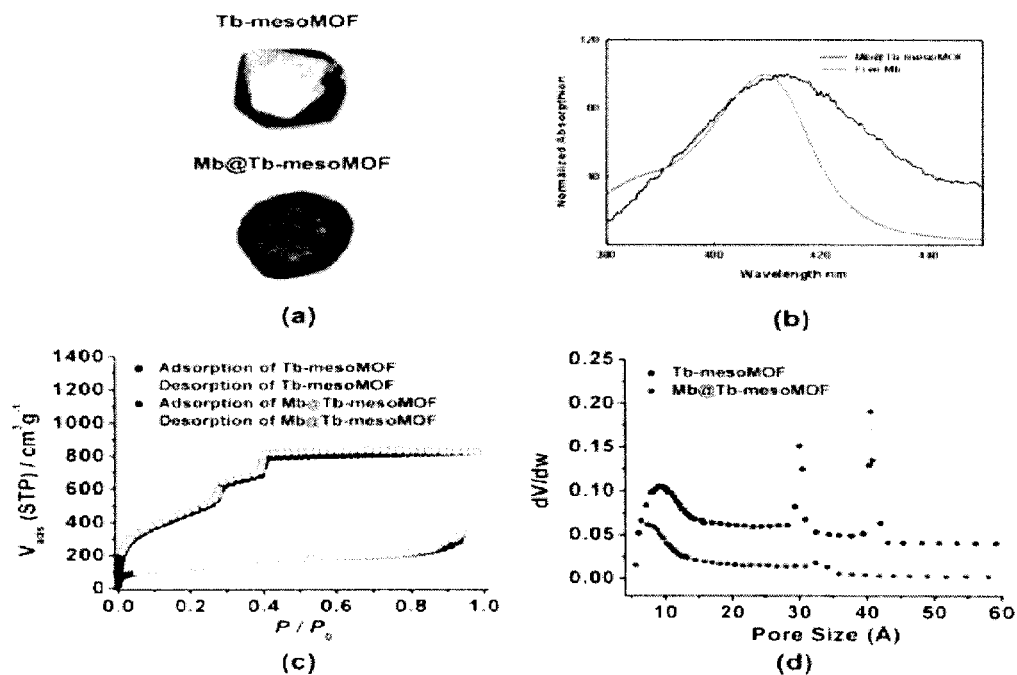
FIG. 3.7

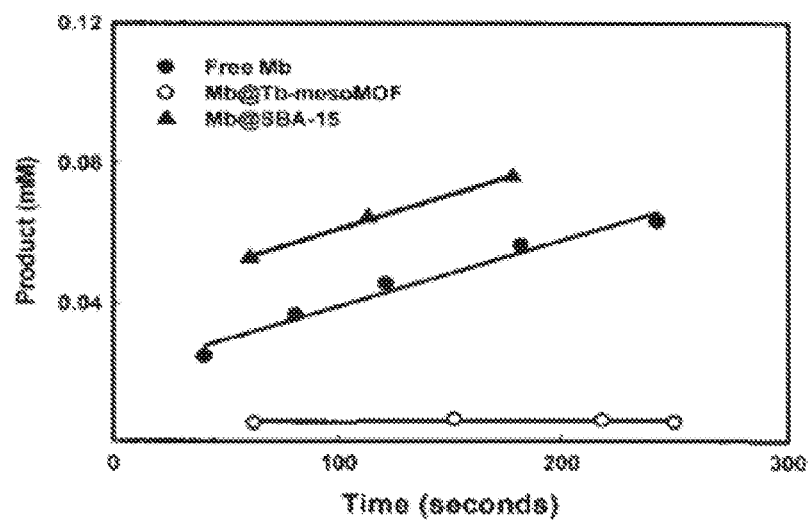
FIG. 3.8A
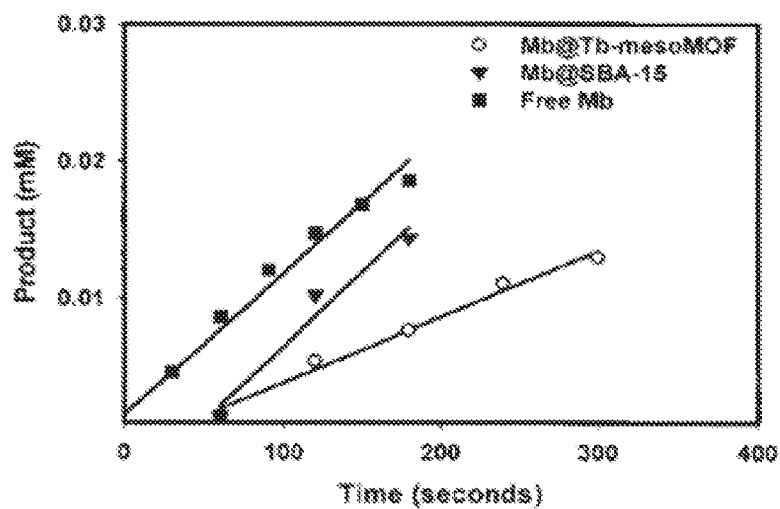
FIG. 3.8B

POLYHEDRAL CAGE-CONTAINING MESOPOROUS METAL-ORGANIC FRAMEWORKS AS PLATFORM FOR BIOCATALYSIS, METHODS OF MAKING THESE FRAMEWORKS, AND METHODS OF USING THESE FRAMEWORKS

CROSS-REFERENCE TO RELATED APPLICATION

This application is the 35 U.S.C. §371 national stage of, and claims priority to and the benefit of, PCT application PCT/US2012/042708, filed Jun. 15, 2012, which claims priority to and the benefit of U.S. Provisional Application No. 61/497,806, filed on Jun. 16, 2011, herein incorporated by reference in its entirety.

BACKGROUND

Biocatalysis has long been of great interest for chemical, pharmaceutical, and food industries. However, the successful utilization of proteins/enzymes as biocatalysts for applications in those aspects largely relies on the ability to successfully stabilize them in what is often an unnatural environment while retaining their functions and activities. Immobilization of the biocatalysts on solid supports possesses the advantages of enhanced stability as well as ease separation and facile recovery for reuse. However, current technologies have limitations and therefore alternative supports are needed.

SUMMARY

Embodiments of the present disclosure provide compositions including polyhedral mesoporous metal-organic framework including a biomolecule (e.g., enzyme), methods of making these compositions, methods of use, and the like. An embodiment of the composition, among others, includes: a mesoporous metal-organic framework (MOF) having at least one nanoscopic cage, wherein at least one nanoscopic cage includes a biomolecule (e.g., an enzyme). In an embodiment, the enzyme is selected from the group consisting of: microperoxidase, myoglobin, alcohol dehydrogenase, a-amylase, chloroperoxidase, a-chymotrypsin, glucose oxidase, horseradish peroxidase, laccase, lipase, manganese peroxidase, soybean peroxidase, trypsin, glycosylase, lysozyme, and a combination thereof An embodiment of the mesoporous metal-organic framework (MOF), among others, includes: at least one nanoscopic cage, wherein at least one nanoscopic cage includes an enzyme, wherein a nanoscopic cage has pore sizes larger than about 1.5 nm and a nanoscopic cage diameter larger than about 2 nm, and wherein the mesoporous MOF is stable in water.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1(a) illustrates a molecular structure of MP-11 (obtained from the solution structure of PDB 1OCD). FIG. 1.1(b) illustrates a 3.9 nm-diameter cage, while FIG. 1.1(c) illustrates a 4.7 nm-diameter cage in Tb-mesoMOF.

FIG. 1.2(a) illustartes a $N_2$ sorption isotherms, and FIG. 1.2(b) illustrates a pore size distributions of Tb-mesoMOF and MP-11@Tb-mesoMOF. FIG. 1.2(c) illustrates optical images of Tb-mesoMOF and MP-11@Tb-mesoMOF. FIG. 1.2(d) illustrates a normalized single-crystal absorbance spectrum derived from specular reflectance for MP-11@Tb-mesoMOF (red) and solution optical spectrum for free MP-11 in buffer solution (black).

FIGS. 1.3 illustrates a kinetic traces for the oxidation of DTBC by (FIG. 1.3(a)) free MP-11 in HEPES buffer (0.6 µM); (FIG. 1.3(b)) MP-11@Tb-mesoMOF (2.0 mg), Tb-mesoMOF (2.0 mg), and MP-11@MCM-41 (2.0 mg) in methanol with $H_2O_2$.

FIG. 1.4 illustrates the reaction rates of MP-11@Tb-mesoMOF and MP-11 @MCM-41 at different cycles.

FIG. 1.5 illustrates UV-Vis spectra of MP-11 in the supernatant of MP-11 HEPES buffer immersed with Tb-mesoMOF.

FIG. 1.6 illustrates UV-Vis spectra of MP-11 in the supernatant of MP-11 HEPES buffer immersed with MCM-41.

FIG. 1.7 illustrates kinetic trace for the reaction of MCM-41, which reveals a rate of $5.20 \times 10^{-5}$ mM/sec (the final conversion is 6.0% after 25 hours).

FIG. 1.8 illustrates kinetic traces for the reactions of MP-11@Tb-mesoMOF at different cycles.

FIG. 1.9 illustrates kinetic traces for the reactions of MP-11@MCM-41 at different cycles.

FIG. 1.10 illustrates UV-Vis spectrum of the supernatant for MP-11@MCM-41 assay indicating severe leaching of MP-11.

FIG. 1.11 illustrates PXRD patterns for Tb-mesoMOF, MP-11@Tb-mesoMOF, and MP-11@Tb-mesoMOF after catalytic cycles.

FIG. 1.12 illustrates Table S1: summary of reaction rates at different catalytic cycles.

FIG. 2.1(a) illustrates the molecular structure of myoglobin (PDB 3LR7, ferric horse heart myoglobin). FIG. 2.1(b) illustrates a 3.9 nm-diameter cage, and FIG. 2.1(c) illustrates a 4.7 nm-diameter cage in Tb-mesoMOF.

FIG. 2.2(a) illustrates optical images of Tb-mesoMOF and Mb@Tb-mesoMOF. FIG. 2.2(b) illustrates UV-Vis absorption spectra for Mb@Tb-mesoMOF (black) and free Mb in buffer solution (red). FIG. 2.2(c) illustrates a $N_2$ sorption isotherms, and FIG. 2.2(d) illustrates a pore size distributions of Tb-mesoMOF and Mb@Tb-mesoMOF.

FIG. 2.3 illustrates kinetic traces for the oxidation of ABTS (FIG. 2.3(a)), and THB (FIG. 2.3(b)), by Free Mb, Mb@Tb-mesoMOF, and Mb@SBA-15 with $H_2O_2$ in HEPES buffer.

FIG. 2.4 illustrates the reaction rates of THB oxidation for Mb@Tb-mesoMOF and Mb@SBA-15 at different cycles.

FIG. 2.5 illustrates the uptake of myoglobin for Tb-mesoMOF and SBA-15 in HEPES buffer.

FIG. 2.6(a) illustrates $N_2$ sorption isotherms of SBA-15 at 77 K, which reveals a BET surface area of ~900 $m^2$/g. FIG. 2.6(b) pore size distribution of SBA-15.

FIG. 2.7 illustrates UV-Vis spectrum of the supernatant for Mb@SBA-15 assay, revealing a leaching of free Mb in HEPES buffer.

FIG. 2.8 illustrates Table S1: Summary of reaction rates at different catalytic cycles.

FIG. 3.1(a) illustrates a 3.9 nm-diameter cage (left) and 4.7 nm-diameter cage (right) in Tb-mesoporous MOF. FIG. 3.1(b) illustrates the molecular structure of MP-11 (left) and Myoglobin (right).

FIG. 3.2(a) illustrates $N_2$ sorption isotherms, and FIG. 3.2(b) illustrates pore size distributions of Tb-mesoMOF and MP-11@Tb-mesoMOF. FIG. 3.2(c) illustrates optical images of Tb-mesoMOF and Tb-mesoMOF/MP-11. FIG. 3.2(d) illustrates normalized single-crystal absorbance spectrum for MP-11@Tb-mesoMOF, derived from specular reflectance (red) and solution optical spectrum for free MP-11 in buffer solution (black).

FIG. 3.3 illustrates kinetic traces for the oxidation of DTBC by (FIG. 3.3(a)) free MP-11 in HEPES buffer (0.6 µM); (FIG. 3.3(b)) MP-11@Tb-mesoMOF (2.0 mg), Tb-mesoMOF (2.0 mg), and MP-11@MCM-41 (2.0 mg) with $H_2O_2$.

FIG. 3.4 illustrates reaction rates of MP-11@Tb-mesoMOF and MP-11@MCM-41 at different cycles.

FIG. 3.5 illustrates PXRD patterns for Tb-mesoMOF, MP-11@Tb-mesoMOF, and MP-11@Tb-mesoMOF after catalytic cycles.

FIG. 3.6 illustrates uptake of myoglobin for Tb-mesoMOF and SBA-15 in HEPES buffer.

FIG. 3.7(a) illustrates optical images of Tb-mesoMOF and Mb@Tb-mesoMOF. FIG. 3.7(b) illustrates UV-Vis absorption spectra for Mb@Tb-mesoMOF (black) and free Mb in buffer solution (red). FIG. 3.7(c) illustrates $N_2$ sorption isotherms. FIG. 3.7(d) illustrates pore size distributions of Tb-mesoMOF and Mb@Tb-mesoMOF.

FIGS. 3.8 illustrate kinetic traces for the oxidation of ABTS (FIG. 3.8(a)), and THB (FIG. 3.8(b)), by Free Mb, Mb@Tb-mesoMOF, and Mb@SBA-15 with $H_2O_2$ in HEPES buffer.

DISCUSSION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Discussion

Embodiments of the present disclosure provide compositions including polyhedral mesoporous metal-organic framework including a biomolecule (e.g., enzyme), methods of making these compositions, methods of use, and the like.

An embodiment of the present disclosure can be used as a biocatalyst since the biomolecule disposed in nanocages of the polyhedral mesoporous metal-organic framework is an enzyme. In particular, embodiments of the present disclosure may have catalytic properties that surpass their mesoporous silica counterparts. In an embodiment, the polyhedral mesoporous metal-organic framework exhibited unprecedented size-selective biocatalysis and superior catalytic activities toward small substrate oxidative substrates. In addition, embodiments of the present disclosure show enhanced stability in multiple solvents and excellent recyclability. Furthermore, embodiments of the present disclosure could be used as a catalyst in organic solvents. Additional details are described herein and in the Examples.

Metal-organic frameworks represent a new class of functional materials. In an embodiment, the metal-organic frameworks can be highly crystalline three dimensional inorganic-organic hybrids constructed by assembling metal ions or small metal-containing clusters with multidentate organic ligands (e.g., carboxylates, tetrazolates, sulfonates) via coordination bonds. Metal-organic frameworks are materials in which metal to organic ligand interactions can form a porous coordination network. Metal-organic frameworks are coordination polymers with an inorganic-organic hybrid frame comprising metal ions or clusters of metal ions and organic ligands coordinated with the metal ions and/or clusters. These materials are organized in a one-, two- or three-dimensional framework in which the metal clusters are linked to one another periodically by bridging ligands and/or pillar ligands. In an embodiment, the inorganic sections can be referred to as secondary building units (SBU) and these can include the metal or metal clusters and bridging ligands. SBUs can be connected by pillar ligands (and/or hybrid pillar/bridging ligands) to form the MOFs. Typically these materials have a crystal structure. In an embodiment, the polyhedral mesoporous MOF can be stable in water.

In an embodiment, the nanoscopic cage of the mesoporous MOF can have a diameter of about 2 to 50 nm. In an embodiment, the mesoporous MOF have a pore size of about 2 nm to 50 nm.

The term "metal" as used within the scope of the present disclosure can refer to metal, metal ions, and/or clusters of metal or metal ions, that are able to form a metal-organic, porous framework material. In an embodiment, the metal can include metals corresponding to the Ia, IIa, IIIa, IVa to VIIIa and Ib and VIb groups of the periodic table of the elements. In an embodiment, the metal (or metal ion) can include: Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, TI, Si, Ge, Sn, Pb, As, Sb and Bi, as well as di-metals. In an embodiment, the metal ion can have a 1+, 2+, 3+, 4+, 5+, 6+, 7+, or 8+ charge.

In an embodiment, the bridging ligands (e.g., coordinating to the metal or metal cluster) and/or the pillar ligands (e.g., linking layers of the MOF) can include one or more functional groups that can coordinate with the metal(s) and/or link metal containing groups (e.g., some ligands can act as bridging ligands and pillar ligands). In an embodiment, the functional group can include —$CO_2H$, —$CS_2H$, —$NO_2$, —$B(OH)_2$, —$SO_3H$, and the like, and combinations thereof. In an embodiment, the functional groups can be bonded to organic compound so that they capable of forming the coordinative bond and of producing the framework material of the MOF. In an embodiment, the organic compound can include a saturated or unsaturated aliphatic compound (e.g., alkane, alkene, and the like having 2 to 20 carbons) or an aromatic compound (e.g., having 4 to 8 carbons per ring) or a compound which is both aliphatic and aromatic.

In an embodiment, the organic compound can include a polycarboxylated ligand (e.g., dicarboxylate ligand, tricarboxylate ligand, or tetra/hexa/octa-carboxylate ligand), a polypyridyl ligand (e.g., dipyridyl ligand, tripyridyl ligand, or tetra/hexa/octa-pyridyl ligand), a polycyano ligand (e.g., dicyano ligand, tricyano ligand, or tetra/hexa/octa-cyano ligand), a polyphosphonate ligand (e.g., diphosphonate ligand, triphosphonate ligand, or tetra/hexa/octa-phosphonate ligand), a polyhydroxyl ligand (e.g., dihydroxyl ligand, trihydroxyl ligand, or tetra/hexa/octa-hydroxyl ligand), a polysulfonate ligand (e.g., disulfonate ligand, trisulfonate ligand, or tetra/hexa/octa-sulfonate ligand), a polyimidazolate, ligand (e.g., diimidazolate ligand, triimidazolate ligand, or tetra/hexa/octa-imidazolate ligand), a polytriazolate (both 1,2,3 and 1,2,4) ligand (e.g., ditriazolate ligand, tritriazolate ligand, or tetra/hexa/octa-triazolate ligands), polytetrazolate ligand (e.g., ditetrazolate ligand, tritetrazolate ligand, or tetra/hexa/octa-tetrazolate ligands), polypyrazolate ligand (e.g., dipyrazolate ligand, tripyrazolate ligand, or tetra/hexa/octa-pyrazolate ligands), and mixtures and combinations thereof.

As noted above, an embodiment of the present disclosure includes a composition including a mesoporous metal-organic framework (MOF) including a biomolecule such as an enzyme (e.g., microperoxidase-11, myoglobin, and the like). In an embodiment, the mesoporous MOF includes one or more types of nanoscopic cages, where one or more of the nanoscopic cages include a biomolecule. In an embodiment, the nanoscopic cage of the mesoporous MOF can have a diameter of about 2 to 20 nm. Embodiments of the nanoscopic cages can provide ideal room to accommodate biomolecules, thus affording better biocatalysis performances compared to the silica counterparts.

In an embodiment, the mesoporous MOF can be a MOF with pore sizes larger than about 1.5 nm and cage diameters larger than about 2 nm, such as: MIL-101 (*Science* 309, 2040 (2005), which is incorporated herein by reference) with cages of about 3.2 nm-diameter, MIL-101 NDC with cages of about 3.5 nm-diameter (Angew. Chem. Int. Ed. 2009, 48, 3791-3794, which is incorporated herein by reference)), JUC-48 (Angew. Chem. Int. Ed. 2007, 46, 6638-6642, which is incorporated herein by reference)) with pore sizes of about 2.8 nm, DUT-9 with pore sizes of about 2.6 nm (Angew. Chem. Int. Ed. 2010, 49, 8489-8492, which is incorporated herein by reference)), STA-16 with pore sizes of about 1.8 nm (J. Am. Chem. Soc. 2011, 133, 1266-1269 which is incorporated herein by reference)), MOF-74 III, IV, V, VI, VII, IX, XI with pore sizes from about 1.5 nm to 10 nm (*Science*, 2012, 336, 6084, 1018-1023 which is incorporated herein by reference)), and MOF-545 with pore size of 3.6 nm (dx.doi.org/10.1021/ic300825s).

In an embodiment, the biomolecules can include enzymes such as microperoxidase, myoglobin, alcohol dehydrogenase, a-amylase, chloroperoxidase, a-chymotrypsin, glucose oxidase, horseradish peroxidase, laccase, lipase, manganese peroxidase, soybean peroxidase, trypsin, glycosylase, lysozyme, and the like. In particular, the enzyme is selected from microperoxidase and myoglobin. In an embodiment, the MOF can be loaded with the biomolecule in amount of about 1 to 1000 μmol/g.

In an embodiment, the MOF including the biomolecule can be made using methods described herein. Specific embodiments are described in the Examples.

In an embodiment, the MOF and the biomolecule are mixed in a buffer (e.g., HEPES, MES buffer (2-(N-morpholino)ethanesulfonic acid), tris buffer, CHES buffer, CAPS buffer, phosphate buffered saline (PBS buffer), or the like) and incubated for about 10 to 150 hours at about 37° C. (e.g., about 6-9 pH range). In an embodiment, the incubation time can be altered to adjust the loading of the biomolecule. In an embodiment, the concentration of the MOF and the biomolecule can be adjusted to obtain the desired loading of the biomolecule. Examples of concentrations are described in the Examples.

Embodiments of the present disclosure can be used in catalytic reactions such as oxidation, hydrolysis, esterification, ethanolysis, digestion of the proteins, dehydrogenation, epoxidation, hydroxylation, amination, and alkylation reactions, or hydrolyzation. Exemplary catalytic reactions are described in the Examples.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Brief Introduction:

Microperoxidase-11 has for the first time been successfully immobilized into a mesoporous MOF consisting of nanoscopic cages and it demonstrates superior enzymatic catalysis performances compared to its mesoporous silica counterpart.

Discussion:

Enzymes are nature's catalysts, featuring high reactivity, selectivity, and specificity under mild conditions.[1] Enzymatic catalysis has long been of great interest to chemical, pharmaceutical, and food industries.[2] However, the use of enzymes for industrial applications is often handicapped by their low operational stability, difficult recovery, and lack of reusability under operational conditions.[3] Immobilization of enzymes on solid supports can enhance enzyme stability as well as facilitate separation and recovery for reuse while maintaining activity and selectivity.[4] In this content, extensive attention has been paid to immobilizing enzymes into mesoporous silica materials that offer high surface areas with tunable, uniform pores.[3,4] Nevertheless, due to the lack of specific interactions with enzyme molecules, mesoporous silica materials suffer from leaching of the immobilized enzyme during the reaction process, which in return results in loss of activity upon reuse.[3,4] Although post-synthetic modification of pore walls with functional organic groups which can provide specific interactions with the immobilized enzymes, has been widely pursued as a strategy to prevent leaching, this inevitably leads to significant decrease of enzyme loading and/or blockage of the channels.[4] Several attributes have been delineated for an ideal host matrix: (i) a hierarchy of pore sizes including large pores for enzyme ingress and small pores to allow diffusion of reactants and products; (ii) high surface area to ensure a high enzyme loading; (iii) large cages decorated with functional organic groups that interact with enzyme molecules and prevent leaching; and (iv) sustained framework integrity under typical reaction conditions.[4]

Over the past decade, a new type of porous materials, porous metal-organic frameworks (MOFs), has emerged.[5] Their amenability to be designed with specific functionality together with their extra-large surface areas not only makes them stand out of traditional porous materials,[6] but also promises great potential for applications such as gas storage/separation,[7] sensor,[8] magnetism,[9] and catalysis.[10] That their nanoscale features can be decorated with functional organic groups for specific interactions with biomolecules makes them appealing to stabilize enzymes for catalytic applications.[11] Although small catalytically active guest species such as organometallic compounds[12] and metalloporphyrins[13] have been successfully encapsulated into porous MOFs, the micropore size of most MOFs precludes the entry of larger-sized enzymes and could result in only surface adsorption.[14] Nevertheless, recent advances in mesoporous MOFs[15] may provide opportunities for enzymatic catalysis although, to the best of our knowledge, the exploration of mesoporous MOFs for enzymatic catalysis applications has not yet been exploited. In this contribution, we demonstrate the successful immobilization and characterization of microperoxidase-11 (MP-11) into a mesoporous MOF, and the resulting MP-11@mesoMOF exhibits superior enzymatic catalysis performances compared to the mesoporous silica counterpart.

MP-11 has dimensions of about 3.3×1.7×1.1 nm.[16] It includes of an iron-heme group linked with an α-helical undecapeptide chain via two thioether bonds of cysteine residues and a coordinated histidine residue at an axial position of the Fe(III)-heme center (FIG. 1.1a). It is able to oxidize a wide range of organic molecules using hydrogen peroxide.[17] The mesoporous MOF we selected for MP-11 immobilization was a recently reported porous MOF,[18] Tb-TATB (hereafter denoted Tb-mesoMOF), which contains nanoscopic cages of 3.9 and 4.7 nm in diameter (FIG. 1.1b, 1.1c). It exhibits characteristic type-IV $N_2$ sorption isotherms (FIG. 1.2a) with pore sizes dominantly distributed around 3.0 and 4.1 nm in addition to a small portion of micropore size around 0.9 nm (FIG. 1.2b). These nanoscopic cages provide adequate space to accommodate MP-11, which should be able to enter Tb-mesoMOF through the mesopores of 3.0 and 4.1 nm.

To immobilize MP-11, freshly synthesized Tb-mesoMOF crystals were immersed in MP-11 solution of HEPES (4-(2-hydroxyethyl)-1-piperazineethanesulfonic acid) buffer, and placed in an incubator at 37° C. The uptake of MP-11 by Tb-mesoMOF was monitored by the disappearance the Soret band at 400 nm in the supernatant,[19] and a loading of 19.1 μmol/g was reached after ~50 hours. The MP-11 saturated Tb-mesoMOF sample (hereafter denoted MP-11@Tb-mesoMOF) was then washed with fresh buffer solution several times until the supernatant became colorless to fully remove the surface adsorbed MP-11. As displayed in FIG. 1.2c, the color of Tb-mesoMOF crystals turns dark red after being saturated with MP-11. Single crystal optical absorption spectroscopy studies revealed that the spectra of MP-11@Tb-mesoMOF exhibit a Soret band at ~410 nm while the corresponding Soret band of MP-11 in buffer solution is 400 nm (FIG. 1.2d); the bathochromic shift of the encapsulated MP-11 in the Tb-mesoMOF is indicative of the interactions between the trapped MP-11 molecules and the hydrophobic nanoscopic cages.[20] $N_2$ sorption isotherms (FIG. 1.2a) measured at 77 K indicated that the BET surface area of Tb-mesoMOF decreases from 1935 m$^2$/g (Langmuir surface 3247 m$^2$/g) to 400 m$^2$/g (Langmuir surface 615 m$^2$/g) after saturation with MP-11, indicating a majority of the free space in Tb-mesoMOF is occupied by MP-11 molecules. Pore size distribution analysis revealed that the pore size of MP-11@Tb-mesoMOF is predominately around 0.9 nm while the pores of 4.1 nm and 3.0 nm observed in Tb-mesoMOF disappeared (FIG. 1.2b). We inferred from these observations that MP-11 molecules should reside in the nanoscopic cages after saturation, while the remaining micropores of 0.9 nm can provide a mechanism for substrates to access the active MP-11 centers housed therein.

MP-11 is well-known to conduct peroxidation of organic molecules by the use of hydrogen peroxide.[17] Unfortunately, free MP-11 tends to aggregate in solution, which leads to less accessibility for the heme, thus adversely affecting its activity.[21] Immobilization in a suitable host material prevents aggregation, renders the heme more accessible to substrates,[22] and allows a broad range of solution conditions. Mesoporous silica materials have been widely investigated for enzyme immobilization;[3,4] and we selected MCM-41 for comparison. MCM-41 adsorbs MP-11 (hereafter denoted MP-11@MCM-41) with a lower loading capacity of 3.4 μmol/g presumably due to its lower surface area (BET surface area: ~1000 m$^2$/g) compared to Tb-mesoMOF. Catalytic experiments were performed for MP-11@Tb-mesoMOF, MP-11@MCM-41, free MP-11, and Tb-mesoMOF.

As polyphenols are routinely used to evaluate the peroxidase activity of porphyrin catalysts,[23] the catalytic activities of MP-11@Tb-mesoMOF and MP-11@MCM-41 were assessed by monitoring the oxidation of the chromogenic substrate 3,5-di-t-butyl-catechol (DTBC) at 420 nm for the formation of the corresponding o-quinone product (Scheme 1).[23] The reactions for MP-11@Tb-mesoMOF, MP-11@MCM-41, and Tb-mesoMOF were performed at room temperature in methanol solution with $H_2O_2$ added, while the catalytic activity of free MP-11 was investigated in HEPES buffer due to its insolubility and complete inactivity in methanol.

Scheme 1. Reaction scheme for oxidation of 3,5-di-t-butyl-catechol to o-quinone.

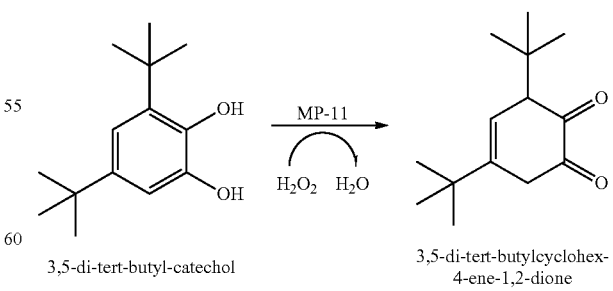

3,5-di-tert-butyl-catechol 3,5-di-tert-butylcyclohex-4-ene-1,2-dione

Free MP-11 in HEPES buffer solution demonstrates a fast initial rate of 8.93×10$^{-4}$ mM/sec (FIG. 1.3a; Table 1) as derived from the slope in the first two minutes. However, it starts to lose activity after only three minutes due to the aggregation in solution.[21] Without MP-11, the reaction for Tb-mesoMOF is going very slowly with a rate of only $2.62\times10^{-6}$ mM/sec; in comparison, MP-11@MCM-41 reacts more than ten times faster with a rate of $3.57\times10^{-5}$ mM/sec (without MP-11, MCM-41 also demonstrates a very slow reaction rate as shown in FIG. 1.7). A even higher rate of $7.58\times10^{-5}$ mM/sec is observed for MP-11@Tb-mesoMOF during the initial time period of ~30 minutes (FIG. 1.3b, Table 1).

TABLE 1

Summary of catalysis results of oxidizing DTBC to o-quinone in the presence of 10 mM $H_2O_2$ in methanol.

|  | Free MP-11[a] | Tb-mesoMOF | MP-11@MCM-41 | MP-11@Tb-mesoMOF |
|---|---|---|---|---|
| Rate[b] (mM/sec) | $8.93\times10^{-4[c]}$ | $2.62\times10^{-6}$ | $3.57\times10^{-5}$ | $7.58\times10^{-5}$ |
| Conversion[d] (%) | 12.3 | 12.2 | 17.0 | 48.7 |

[a]Diluted to 0.6 μM in HEPES buffer;
[b]rate calculated from the first 30 minutes;
[c]Initial rate calculated in the first two minutes;
[d]final conversion after 25 hours.

After 25 hours, no more o-quinone was generated, and a low final conversion of 12.3% was found for free MP-11 in buffer solution, which can be ascribed to the fast deactivation of MP-11 as a result of aggregation in solution. A final conversion of 12.2% was observed for Tb-mesoMOF in methanol solution, meaning Tb-mesoMOF exhibits low activity for the oxidation of DTBC to o-quinone. MP-11@MCM-41 demonstrated an enhanced activity with a final conversion of 17.0%, but the catalyst was bleached out owing to the leaching of MP-11 during the assay (FIG. 1.10). In contrast, the color of MP-11@Tb-mesoMOF remained dark red with no MP-11 found in the supernatant after the reaction, and a much higher conversion of 48.7% was obtained. These experiments indicate that the microperoxidase catalyst was greatly stabilized through the mesoporous MOF host matrix.

We evaluated the recyclability of MP-11@Tb-mesoMOF by checking its catalytic activities at different cycles. As shown in FIG. 1.4, the reaction rates of MP-11@Tb-mesoMOF fluctuate from $5.40\times10^{-5}$ mM/sec to $8.34\times10^{-5}$ mM/sec in the first six cycles; it decreases to $3.56\times10^{-5}$ mM/sec at the seventh cycle, representing ~53% activity drop compared to that of the first cycle (FIG. 1.12, Table S1). In comparison, the activity of MP-11@MCM-41 decreases abruptly with more than 60% activity lost after the first cycle, and only 28% activity remains at the third cycle (Table S1). The fast decay of MP-11@MCM-41 originates from the leaching of MP-11, which was detected in the supernatant (FIG. 1.10). No MP-11 leaching was observed for MP-11@Tb-mesoMOF over seven cycles, and the Tb-mesoMOF host could still maintain its framework integrity after catalytic cycles as evidenced by the powder X-ray diffraction studies (FIG. 1.11). We reasoned that the capability of MP-11@Tb-mesoMOF to retain activity for at least six cycles could be attributed to the strong hydrophobic interactions between the Tb-mesoMOF framework and MP-11 molecules trapped in the hydrophobic nanoscopic cages, preventing their escape from the MOF host matrix.

In summary, we have demonstrated for the first time the successful immobilization of microperoxidase-11 into a mesoporous MOF consisting of nanoscopic cages, which exhibited superior enzymatic catalysis performances compared to mesoporous silica material MCM-41. The high catalytic activity together with recyclability and solvent adaptability for MP-11 encapsulated in the Tb-mesoMOF with a well-defined structure promises that mesoporous MOFs might serve as a new type of host matrix material to immobilize enzymes for catalysis applications in organic solvents. Considering the richness of mesoporous MOF structures, the present studies also open a new avenue for enzyme immobilization as heterogenous bio-catalysists. Ongoing work in our laboratory is exploring and designing new mesoporous MOFs to immobilize different kinds of enzymes for catalysis applications under various conditions.

References, Each of Which is Incorporated Herein by Reference (1) Reedy, C. J.; Gibney, B. R. *Chem. Rev.* 2004, 104, 617-650.
(2) Schmid, A.; Dordick, J. S.; Hauer, B.; Kiener, A.; Wubbolts, M.; Wtholt, B. *Nature* 2001, 409, 258-268.
(3) Hartmann, M.; Jung, D. *J. Mater. Chem.* 2010, 20, 844-857.
(4) (a) Hartmann, M. *Chem. Mater.* 2005, 17, 4577-4593; (b) Hudson, S.; Cooney, J.; Magner, E. *Angew. Chem. Int. Ed.* 2008, 47, 8582-8594.
(5) Long, J. R.; Yaghi, O. M. *Chem. Soc. Rev.* 2009, 38, 1213-1214.
(6) (a) Kitagawa, S.; Kitaura, R.; Noro, S.-i. *Angew. Chem. Int. Ed.* 2004, 43, 2334-2375; (b) Morris, R. E.; Wheatley, P. S. *Angew. Chem. Int. Ed.* 2008, 47, 4966-4981; (c) Férey, G. *Chem. Soc. Rev.* 2008, 37, 191-214; (d) Ma, S.; Zhou, H.-C. *Chem. Comm.*, 2010, 46, 44-53; (e) S. Ma, L. Meng, *Pure & Appl. Chem.*, 2011, 83, 167-188.
(7) (a) Ma, S. *Pure & Appl. Chem.*, 2009, 81, 2235-2251; (b) Li, J.-R.; Kuppler, R. J.; Zhou, H.-C. *Chem. Soc. Rev.* 2009, 38, 1477-1504; (c) Murray, L. J.; Dinca, M.; Long, J. R. *Chem. Soc. Rev.* 2009, 38, 1294-1314.
(8) (a) Allendorf, M. D.; Bauer, C. A.; Bhakta, R. K.; Houk, R. J. T. *Chem. Soc. Rev.* 2009, 38, 1330-1352; (b) Lan, A. J.; Li, K. H.; Wu, H. H.; Olson, D. H.; Emge, T. J.; Ki, W.; Hong, M. C.; Li, J. *Angew. Chem. Int. Ed.* 2009, 48, 2334-2338. (c) Chen, B.; Xiang, S.; Qian, G. *Acc. Chem. Res.* 2010, 43, 1115-1124.
(9) Kurmoo, M. *Chem. Soc. Rev.* 2009, 38, 1353-1379.
(10) (a) Lee, J.; Farha, O. K.; Roberts, J.; Scheidt, K. A.; Nguyen, S. T.; Hupp, J. T. *Chem. Soc. Rev.* 2009, 38, 1450-1459; (b) Ma, L. Q.; Abney, C.; Lin, W. B. *Chem. Soc. Rev.* 2009, 38, 1248-1256; (c) Corma, A.; Garcia, H.; Llabreés i Xamena, F. X. *Chem. Rev.* 2010, 110, 4606-4655.
(11) (a) Perry, J. J.; Perman, J. A.; Zaworotko, M. J. *Chem. Soc. Rev.* 2009, 38, 1400-1417; (b) Tanabe, K. K.; Cohen, S. M. *Chem. Soc. Rev.* 2011, 40, 498-519.
(12) Hermes, S.; Schröter, M.-K.; Schmid, R.; Jhodeir, L.; Muhler, M.; Tissler, A.; Fischer, R. W.; Fischer, R. A. *Angew. Chem. Int. Ed.* 2005, 44, 6237-6240.
(13) (a) Alkordi, M. H.; Liu, Y. L.; Larsen, R. W.; Eubank, J. F.; Eddaoudi, M. *J. Am. Chem. Soc.* 2008, 130, 12639-12641; (b) Kockrick, E.; Lescouet, T.; Kudrik, E. V.; Sorokin, A. B.; Farrusseng, D. *Chem. Commun.* 2011, 47, 1562-1564.
(14) Pisklak, T. J.; Macias, M.; Coutinho, D. H.; Huang, R. S.; Balkus, K. J. *Top. Catal.* 2006, 38, 269-278.
(15) Fang, Q.-R.; Makal, T. A.; Young, M. D.; Zhou, H.-C. *Comment Inorg. Chem.* 2010, 31, 165-195.
(16) Marques, H. *Dalton Trans.* 2007, 39, 4371-4385.
(17) Veeger, C. J. Inorg. Biochem. 2002, 91, 35-45.
(18) Park, Y. K.; Choi, S. B.; Kim, H.; Kim, K.; Won, B.-H.; Choi, K.; Choi, J.-S.; Ahn, W.-S.; Won, N.;

Kim, S.; Jung, D. H.; Choi, S.- H.; Kim, G.- H.; Cha, S.-S.; Jhon, Y. H.; Yang, J. K.; Kim, J. *Angew. Chem. Int. Ed.* 2007, 46, 8230-8233.

(19) Nakamura, S.; Mashino, T.; Hirobe, M.; *Tetrahedron Lett.* 1992, 33, 5409-5412.

(20) Uchida, T.; Ishimori, K.; Morishima, I. *J. Biol. Chem.* 1997, 272, 30108-30114.

(21) Kadnikova, E. N.; Kostic, N. M. *J. Org. Chem.* 2003, 68, 2600-2608.

(22) Yan, A. X.; Li, X. W.; Ye, Y. H. Appl. *Biochem. Biotechnol.* 2002, 101, 113-129.

(23) Kawamura-Konishi, Y.; Asano, A.; Yamazaki, M. Tashiro, H.; Suzuki, H. J. *Mol. Catal. B-Enzym.* 1998, 4, 181-190.

Supplemental Material for Example 1:
Synthesis of Tb-mesoMOF:

Crystalline samples of Tb-mesoMOF were prepared according to the procedures reported in ref. 1.

MP-11 Uptake Experiments:

MP-11(Sigma) prepared in HEPES buffer was added into Tb-mesoMOF and incubated at 37° C. The supernatant was scanned at different time points to determine uptake of MP-11 by the decrease of the Soret band at 400 nm ($\epsilon$=176 mM$^{-1}$ cm$^{-1}$)$^2$, and a saturation was found after 50 hours (Elemental analysis for Tb-mesoMOF: C, 41.59%; H, 3.35%; N, 5.92%; MP-11@Tb-mesoMOF: C, 42.87%; H, 4.88%; N, 8.09%). For MCM-41 (Sigma), the same procedures and conditions were followed using MP-11 and incubation time of 97 hours to achieve saturation. For each preparation, a sample of the initial MP-11 solution was also incubated under the same conditions and was used to determine the reference concentrations and spectra. The saturated samples were then washed with fresh HEPES buffer solution several times till the supernatant became colorless to fully remove the surface adsorbed MP-11. (See FIGS. 1.5 to 1.12)

Examination of the catalytic activities:

The initial rates of oxidation of DTBC by various catalysts discussed in this work (~2.0 mg) in the presence of 10 mM $H_2O_2$ in methanol solution were determined on a Varian Cary50 spectrophotometer. The oxidation of the substrate to the corresponding o-quinone dimer product was directly monitored at 420 nm ($\epsilon$=1,910 M$^{-1}$cm$^{-1}$)$^3$ by taking the absorption spectra of the supernatant solution at various time points in the reaction.

Very dilute solution of MP-11 (0.6 µM) in HEPES buffer instead was used to check the optimal catalytic activity of MP-11 under the same catalytic conditions as above since MP-11 is insoluble in methanol.

Single-Crystal Specular Reflectance Spectroscopy.

Single-crystal UV-Vis absorbance spectra were obtained with a polarized specular reflectance microspectrophotometer.[4] Single crystals of MP11@Tb-mesoMOF (about 0.1 mm on a side) and pure Tb-mesoMOF (about 0.1 mm on a side) were mounted on glass fibers with Duco cement, the fiber in turn on a mounting pin and affixed in a standard X-ray gonoimeter head. The natural, reflective crystal surfaces were oriented normal to the incident light in the spectrophotometer. The light source was a 75-W xenon arc lamp and all instrument optics is reflective except the polarizer. The reflected light was collected with a cooled CCD and compared to that from a standardized mirror and then processed into absorbance data through Kramers-Kronig transformations.[5]

$N_2$ Sorption Experiments.

$N_2$ sorption isotherms of Tb-mesoMOF and MP-11@Tb-mesoMOF were collected using the surface area analyzer ASAP-2020. Before the measurements, the freshly prepared samples were thoroughly solvent-exchanged with methanol, and activated under dynamic vacuum first at room temperature overnight and then at 120° C. for two hours. The surface area of Tb-mesoMOF is comparable with that reported in ref. 1 for the sample activated at 80° C.

References, each of which is incorporated herein by reference:

(1) Park, Y. K.; Choi, S. B.; Kim, H.; Kim, K.; Won, B.- H.; Choi, K.; Choi, J.- S.; Ahn, W.- S.; Won, N.; Kim, S.; Jung, D. H.; Choi, S.- H.; Kim, G.- H.; Cha, S.- S.; Jhon, Y. H.; Yang, J. K.; Kim, J. *Angew. Chem. Int. Ed.* 2007, 46, 8230.

(2) Nakamura, S.; Mashino, T.; Hirobe, M.; *Tetrahedron Lett.* 1992, 33, 5409.

(3) Kawamura-Konishi, Y.; Asano, A.; Yamazaki, M. Tashiro, H.; Suzuki, H. *J. Mol. Catal. B-Enzym.* 1998, 4, 181.

(4) Musselman, R. L. *Inorg. Chimica Acta.* 2008, 361, 820.

(5) Anex, B. G. *Mol. Cryst.* 1966, 1, 1.

(6) Kronig, R. *J. Opt. Soc. Am.* 1926, 12, 547.

Example 2

Brief Introduction:

Myoglobin has been for the first time successfully immobilized into a mesoporous MOF with hierarchical pore sizes, which demonstrates interesting size-selective biocatalysis performance as well as superior catalytic activities toward small substate oxidation compared to mesoporous silica material counterpart.

Introduction:

Biocatalysis has long been of great interest in both academia and industry.[1] However, the successful utilization of proteins as biocatalysts in chemical, pharmaceutical, and food industries largely relies on the ability to successfully stabilize them in what is often an unnatural environment while retaining their functions and activities.[2] Immobilization of the biocatalysts on solid supports presents the advantages of enhanced stability as well as ease of separation and facile recovery for reuse.[3] In addition, if a solid support possesses a hierarchy of pore sizes with large pores for protein ingress and small pores to allow diffusion of reactants and products, the size-, or shape-selective catalysis which is highly desirable in industry but usually cannot be exhibited by native proteins,[3a] could be expected. Over the past two decades, extensive efforts have been dedicated to the search for various types of host matrix materials, and current attention has been focused on mesoporous silica materials owing to their high surface areas as well as tunable and uniform pores.[2,3] Nevertheless, due to the lack of specific interactions with protein molecules, mesoporous silica materials suffer from leaching during the reaction process, which in return results in loss of activity upon reuse; additionally, no size- and shape-selective catalysis has ever been observed presumably owing to the difficulty to achieve hierarchical pores for mesoporous silica materials.[2,3] These have been recognized as some major hurdles limiting their applications in biocatalysis, thus prompting the search for new types of host matrix materials.[2]

One of the promising host matrix candidates is mesoporous metal-organic framework (MOF) material, which has been advanced in recent years.[4] Compared with mesoporous silica materials, mesoporous MOFs possess higher surface areas and pore walls composed of functional organic groups which could afford specific interactions with protein molecules thus avoiding leaching. In addition, mesoporous MOFs can be tailored to possess hierarchical pores with mesopores to accommodate biomolecules and micropores to selectively allow diffusion of reactants and products thus possibly resulting in size-, or shape-selective catalysis.

Recently, we showed for the first time the successful immobilization of the "micro-enzyme" MP-11 into a mesoporous MOF, which exhibited superior enzymatic catalysis performance compared to mesoporous silica material.[5] Although the small MP-11 is not a real protein molecule despite its enzymatic peroxidation function,[6] this work paved the first step to develop mesoporous MOFs as a new type of host matrix materials for biocatalysis application and also encouraged us to explore the possibility to immobilize protein molecules into mesoporous MOFs.

Herein, we selected myoglobin (Mb), which is a small oxygen binding protein of muscle cells with a molecular dimension of about 2.1×3.5×4.4 nm.[7] It contains a single polypeptide chain of 153 amino acid residues and a heme prosthetic group in a hydrophobic pocket (FIG. 2.1a).[8] The biocatalytic performances of Mb are usually evaluated through its peroxidative activity which originates from the heme prosthetic group.[9] Considering its stability in buffer solutions, we continue to employ the recently reported mesoporous MOF, Tb-mesoMOF as host matrix for the "proof of concept" studies on immobilizing Mb protein molecules. Crystallographically, Tb-mesoMOF consists of nanoscopic cages of 3.9 and 4.7 nm in diameter (FIG. 2.1b, 2.1c),[10] and features type-IV sorption behavior with hierarchical pore sizes of 0.9 nm, 3.0 nm and 4.1 nm as revealed by $N_2$ gas sorption studies at 77 K.[5] Since Mb molecule possesses highly dynamic and flexible structure, we expect that it could squeeze into Tb-mesoMOF through the mesopores via a specific orientation, and the 4.7 nm-diameter cages may serve as the ideal room to accommodate the Mb molecules Indeed, Mb can be immobilized into the mesoporous MOF in spite of its apparent larger molecular size than the pore sizes of Tb-mesoMOF. The resulting Mb@Tb-mesoMOF not only exhibited superior biocatalytic performances compared to the mesoporous silica counterpart, but also demonstrated interesting size-selective biocatalysis due to the hierarchical pore sizes of the Tb-mesoMOF.

Experimental Section

Materials Syntheses

Crystalline samples of the mesoporous MOF, Tb-mesoMOF and the mesoporous silica material, SBA-15 were prepared according to the procedures reported in ref. 10 and ref. 11 respectively.

Myoglobin Uptake Experiments

Typically 2.5 mg/mL of met-myoglobin from equine skeletal muscle (Sigma) was prepared in 2.0 mL 4-(2-hydroxyethyl)-1-piperazineethanesulfonic acid (HEPES) buffer added into 5.0 mg of Tb-mesoMOF and incubated at 37° C. for 94 hours. The protein concentration in the supernatant was determined at different time points using the BCA method of protein determination (Bicinchoninic Acid protein assay using bovine serum albumin as the standard) in order to establish the uptake of Mb.[12] For the SBA-15 (5.0 mg) the same procedure and conditions were followed. For each preparation, a sample of the Mb solution was also incubated under the same conditions and was used to determine the reference concentrations.

Examination of the Catalytic Activities

The initial rates for $ABTS^{+\cdot}$ formation were monitored using 0.5 mM 2,2' azinodi(3-ethylbenzthiazoline)-6-sulfonate (ABTS) in presence of 10 mM $H_2O_2$ in HEPES buffer by various catalysts discussed in this work (~5 mg used for each solid catalyst and 0.5 μM in HEPES buffer for free Mb) on a Varian CARY50 spectrophotometer. The oxidation of the substrate to the corresponding oxidized product $ABTS^{+\cdot}$ was directly monitored at 660 nm ($\epsilon=12\,M^{-1}cm^{-1}$)[13] by taking the absorption spectra of the supernatant solution at various time points over the reaction.

The initial rates of trihydroxybenzene (THB) oxidation were monitored using 0.5 mM THB in presence of 10 mM $H_2O_2$ in HEPES buffer by various catalysts discussed in this work (~5 mg used for each solid catalyst and 0.5 μM in HEPES buffer for free Mb) also on a Varian CARY50 spectrophotometer. The oxidation of the substrate to the corresponding oxidized product purpurogallin dimer were directly monitored at 320 nm ($\epsilon=31,250\,M^{-1}\,cm^{-1}$)[14] by taking the absorption spectra of the supernatant solution at various time points over the reaction.

$N_2$ Sorption Measurements $N_2$ sorption isotherms of Tb-mesoMOF and Mb@Tb-mesoMOF were collected using the surface area analyzer ASAP-2020. Before the measurements, the freshly prepared samples were thoroughly solvent-exchanged with methanol, and activated under dynamic vacuum first at room temperature overnight and then at 120° C. for two hours. The surface area of Tb-mesoMOF is comparable with that reported in ref. 10 for the sample activated at 80° C.

Results and Discussion

To explore the possibility to immobilize the large Mb protein molecule, freshly prepared Tb-mesoMOF crystals were immersed in Mb solution of 4-(2-hydroxyethyl)-1-piperazineethanesulfonic acid (HEPES) buffer, and placed in an incubator at 37° C. The uptake of Mb by Tb-mesoMOF at different time points was determined by using the BCA method for protein determination,[12] and a saturated loading of 9.1 μmol/g was reached after ~94 hours (FIG. 2.5, ESI†). The Mb saturated Tb-mesoMOF sample (hereafter denoted Mb@Tb-mesoMOF) was then washed with fresh buffer solution several times until the supernatant became colorless to fully remove loosely attached Mb molecules on the surface. The successful immobilization of large Mb protein molecules into Tb-mesoMOF was confirmed by optical image and UV-Vis spectroscopy studies. As displayed in FIG. 2.2a, the color of Tb-mesoMOF crystal turns dark brown after being saturated with Mb, which strongly indicates the ingress of Mb molecules into Tb-mesoMOF. Solid-state UV-Vis absorption spectroscopy studies revealed that Mb@Tb-mesoMOF exhibited a Soret band at ~412 nm, which represents a slight bathochromic shift compared to the Soret band of ~410 nm for Mb in buffer solution (FIG. 2.2b), indicating the interactions between the trapped Mb molecules and the framework of Tb-mesoMOF.[15] $N_2$ sorption isotherms (FIG. 2.2c) measured at 77 K indicated that the BET surface area of Tb-mesoMOF decreases from 1935 $m^2/g$ (Langmuir surface 3247 $m^2/g$) to 462 $m^2/g$ (Langmuir surface 642 $m^2/g$) after saturation with Mb. Pore size distribution analysis revealed that the pore size of Mb@Tb-mesoMOF is predominately around 0.8 nm while the pores of 4.1 nm and 3.0 nm observed in Tb-mesoMOF disappeared (FIG. 2.2d). We deduced from these observations that Mb molecules block the two types of mesopores, while the remaining micropores of ~0.8 nm can provide a pathway for small substrates to access the active Mb centers housed in the 4.7 nm-diameter cages. The results from gas sorption studies also support the successful immobilization of Mb into Tb-mesoMOF.

Mb is known to perform peroxidation of organic substrates by the use of hydrogen peroxide,[9] and its peroxidase activity is usually assessed with the assay of 2,2' azinodi(3-ethylbenzthiazoline)-6-sulfonate (ABTS) as a redox indicator by monitoring the rate of increase in absorbance at 660 nm ($\epsilon=12\,mM^{-1}cm^{-1}$ for $ABTS^{+\cdot}$) subsequent to the addition of peroxide (Scheme 1).[13] Since mesoporous silica materials have been widely investigated for protein immobilization,[2,3] we selected SBA-15[11,16] for comparison. SBA-15 with the pore size mono-distributed around 8.5 nm adsorbs Mb (hereafter denoted Mb@SBA-15) with a lower loading capacity of 7.0 µmol/g (FIG. 2.5, ESI†) presumably due to its lower surface area (BET surface area: ~900 m²/g, FIG. 2.6, ESI†) compared to Tb-mesoMOF. Assays of ABTS oxidation were conducted for Mb@Tb-mesoMOF, Mb@SBA-15, and free Mb at room temperature in HEPES buffer.

Scheme 1:
Reaction scheme for oxidation of ABTS by hydrogen peroxide catalyzed by Mb.

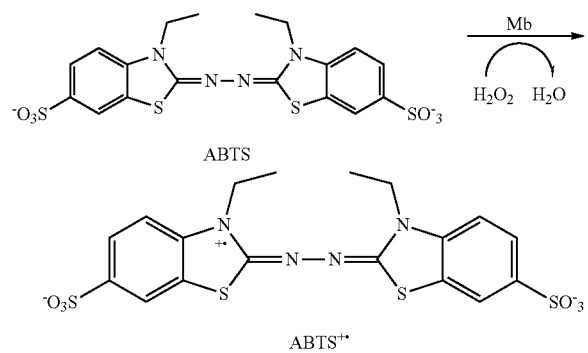

As shown in FIG. 2.3a, free Mb in solution demonstrates a very fast initial rate of $3.27 \times 10^{-4}$ mM/sec for ABTS$^{+\bullet}$ formation as expected; and a high initial rate of $2.00 \times 10^{-4}$ mM/sec is observed for Mb@SBA-15 (Table 1), which is consistent with the values reported in the literatures.[17] However, an extremely low initial rate of $8.33 \times 10^{6}$ mM/sec is found for Mb@Tb-mesoMOF, which is almost inactive for ABTS$^{+\bullet}$ formation despite a larger amount of Mb trapped in Tb-mesoMOF compared to SBA-15. We reasoned that the very low initial rate of Mb@Tb-mesoMOF for ABTS$^{+\bullet}$ formation should be attributed to its small available pore size of ~0.8 nm, which does not allow the large ABTS substrate with a molecular dimension 10.1 Å×17.3 Å to access the active Mb centers housed in Tb-mesoMOF. This prompts us to evaluate its possible size-selective biocatalysis performance by assaying a smaller substrate.

Scheme 2:
Reaction scheme for oxidation of THB by hydrogen peroxide catalyzed by Mb.

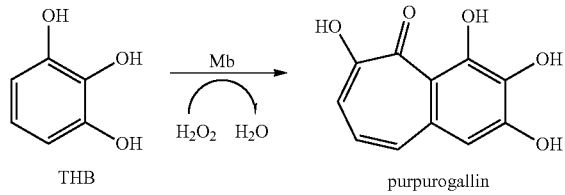

Polyphenols are also routinely used to evaluate the peroxidase activity of Mb, although its activity is about one fourth of the ABTS system.[18] To evaluate the biocatalytic activity as well as to confirm the possible size-selective biocatalysis performance of Mb@Tb-mesoMOF, we selected the small polyphenol 1,2,3-trihydroxybenzene (THB) (or pyrogallol) which has a molecular dimension of 5.7 Å×5.8 Å as the substrate by monitoring its oxidation at 320 nm for the formation of the corresponding purpurogallin dimer product (molecular dimension: 5.8 Å×7.5 Å) (Scheme 2).[14] Given the small substrate molecule can access the active Mb centers through the 0.8 nm pore which can also facilitate the exit of the product molecule, we expected Mb@Tb-mesoMOF should exhibit a much higher activity of oxidizing THB compared to ABTS.

As expected, Mb@Tb-mesoMOF demonstrates a high initial rate of $4.80 \times 10^{-5}$ mM/sec using THB as substrate (FIG. 2.3b, Table 1), which is about half of free Mb with a rate of $1.02 \times 10^{-4}$ mM/sec. The slower initial rate for Mb@Tb-mesoMOF compared to free Mb should originate from the slow diffusion of the substrates from solution into Mb@Tb-mesoMOF through the micropores of 0.8 nm. Whereas the observed high rate of $8.96 \times 10^{-5}$ mM/sec for Mb@SBA-15 can be attributed to the severe leaching of Mb (FIG. 2.7, ESI†), which actually was also responsible for the high initial rate for ABTS$^{+\bullet}$ formation in Mb@SBA-15. Nevertheless, after one hour, Mb@Tb-mesoMOF exhibits a much faster average rate of $1.55 \times 10^{-5}$ mM/sec compared to Mb@SBA-15 (rate: $6.10 \times 10^{-6}$ mM/sec) and free Mb (rate: $8.20 \times 10^{-6}$ mM/sec). These results indicate that Mb@Tb-mesoMOF indeed demonstrates selective biocatalysis of oxidizing small THB over large ABTS due to the size effect, which to the best of our knowledge has never been reported before.

TABLE 1

Summary of catalysis results of oxidizing ABTS and THB in the presence of 10 mM $H_2O_2$ in HEPES buffer.

| | Free Mb[a] | Mb@SBA-15 | Mb@Tb-mesoMOF |
|---|---|---|---|
| Initial rate for ABTS$^{+\bullet}$ formation (mM/sec)[b] | $3.27 \times 10^{-4}$ | $2.00 \times 10^{-4}$ | $8.33 \times 10^{-6}$ |
| Initial rate for THB oxidation[c] (mM/sec) | $1.02 \times 10^{-5}$ | $8.96 \times 10^{-5}$ | $4.80 \times 10^{-5}$ |
| Average Rate for THB oxidation[d] (mM/sec) | $8.20 \times 10^{-6}$ | $6.10 \times 10^{-6}$ | $1.55 \times 10^{-5}$ |

[a]Diluted to 0.5 µM in HEPES buffer;
[b]initial rate calculated in the first four minutes;
[c]initial rate calculated in the first five minutes;
[d]average rate over one hour.

One of the important issues for biocatalysis is the reusability of the catalysts. To evaluate the recyclability of Mb@Tb-mesoMOF, we checked its catalytic activities at different cycles. As shown in FIG. 2.4, the reaction rates of THB oxidation for Mb@Tb-mesoMOF fluctuate from $3.84 \times 10^{-5}$ mM/sec to $4.80 \times 10^{-5}$ mM/sec over fifteen cycles; it slightly decreases to $3.20 \times 10^{-5}$ mM/sec at the sixteenth cycle, representing ~33% activity drop compared to that of the first cycle (FIG. 2.8, Table S1, ESI†). In comparison, the activity of Mb@SBA-15 decreases abruptly with more than 40% activity loss after the first cycle, and less than 18% activity remains at the third cycle (FIG. 2.4, and FIG. 2.8, Table S1). The fast decay of Mb@SBA-15 can be ascribed to the severe leaching of Mb, which was detected in the supernatant (FIG. 2.7, ESI†). No Mb leaching was observed for Mb@Tb-mesoMOF over the sixteen cycles of reactions. We reasoned that the capability of Mb@Tb-mesoMOF to retain activity for at least fifteen cycles could be attributed to the strong interactions between the Tb-mesoMOF framework and the Mb molecules trapped in the 4.7 nm-diameter cages, which prevent their escape from the MOF host matrix. This also suggests that the Mb molecules can be greatly stabilized via the mesoporous MOF host matrix.

Conclusions

In summary, we have demonstrated for the first time the successful immobilization of the protein myoglobin into a mesoporous MOF with hierarchical pore sizes, which exhibited unprecedented size-selective biocatalysis as well as superior catalytic activities toward small substate oxidation compared to mesoporous silica material SBA-15. The interesting size-selective biocatalysis together with enhanced stability and excellent recyclability for Mb encapsulated in the Tb-mesoMOF not only promises that mesoporous MOFs could serve as a new type of host matrix materials to immobilize proteins for industry-related biocatalysis applications, but also makes mesoporous MOFs stand out of traditional host matrix materials for proteins immobilization particularly when considering their structural versatility and design amenability. Ongoing work in our laboratory is investigating the diffusion mechanism of Mb into the Tb-mesoMOF and the specific interactions between the Mb protein molecule and the MOF framework. The exploration and design of new mesoporous MOFs to immobilize different kinds of proteins for biocatalysis applications is currently underway in our laboratory as well.

References, each of which is incorporated herein by reference:

1 A. Schmid, J. S. Dordick, B. Hauer, A. Kiener, M. Wubbolts and B. Witholt, *Nature*, 2001, 409, 258-268.
2 S. Hudson, J. Cooney and E. Magner, Angew. Chem., 2008, 120, 8710-8723; *Angew. Chem. Int. Ed.*, 2008, 47, 8582-8594.
3 a) M. Hartmann, *Chem. Mater.*, 2005, 17, 4577-4593; b) M. Hartmann and D. Jung, *J. Mater. Chem.*, 2010, 20, 844-857.
4 a) J. R. Long and O. M. Yaghi, *Chem. Soc. Rev.*, 2009, 38, 1213-1214; b) Q.- R. Fang, T. A. Makal, M. D. Young and H.- C. Zhou, *Comment Inorg. Chem.*, 2010, 31, 165-195.
5 V. Lykourinou, Y. Chen, X.- S. Wang, L. Meng, T. Hoang, L.- J. Ming, R. L. Musselman and S. Ma, *J. Am. Chem. Soc.*, 2011, 133, 10382-10385.
6 C. Veeger, *J. Inorg. Biochem.*, 2002, 91, 35-45.
7 M. A. Bos, Z. Shervani, A. C. I. Anusiem, M. Giesbers, W. Norde and J. M. Kleijn, *Colloids Surf. B: Biointerfaces.*, 1994, 3, 91-100.
8 D. L. Nelson and M. M. C. Lenin, *Principles in Biochemistry*, Worth Publishers, New York, 2000.
9 T. Itoh, R. Ishii, T. Ebina, T. Hanaoka, Y. Fukushima and F. Mizukami, *Bioconjug. Chem.*, 2006, 17, 236-240.
10 Y. K. Park, S. B. Choi, H. Kim, K. Kim, B.- H. Won, K. Choi, J.- S. Choi, W.- S. Ahn, N. Won, S. Kim, D. H. Jung, S.- H. Choi, G.- H. Kim, S.- S. Cha, Y. H. Jhon, J. K. Yang and J. Kim, *Angew. Chem. Int. Ed.*, 2007, 46, 8230-8233.
11 L. F. Wang, K. F. Lin, Y. Di, D. L. Zhang, C. J. Li, Q. Yang, Chengyang Yin, Z. Sun, D. Jiang and F.- S. Xiao, *Microporous Mesoporous Mater.*, 2005, 86, 81-88.
12 P. K. Smith, R. I. Krohn, G. T. Hermanson, F. H Gartner, E. K. Fujimoto, N. M. Goeke, B. J. Olson and D. C. Klenk, *Anal. Biochem.*, 1985, 150, 76-85.
13 T. McMurry and J. T. Groves, *Cytochrome P450, Structure, Mechanism and Biochemistry*; Ortiz de Montellano, P., Ed.; Plenum: London, 1986.
14 G. D. Thom and L. R. C. Barclay, *Can. J. Chem.*, 1951, 30, 251-256.
15 Y. S. Chaudhary, S. K. Manna, S. Mazumdar and D. Khushalani, *Microporous Mesoporous Mater.*, 2008, 109, 535-541.
17 D. Zhao, J. Feng, Q. Huo, N. Melosh, G. H. Fredrickson, B. F. Chmelka, B. F. Chmelka and G. D. Stucky, *Science*, 1998, 279, 548-552.
15 Y. S. Chaudhary, S. K. Manna, S. Mazumdar and D. Khushalani, *Microporous Mesoporous Mater.*, 2008, 109, 535-541.
16 D. Zhao, J. Feng, Q. Huo, N. Melosh, G. H. Fredrickson, B. F. Chmelka, B. F. Chmelka and G. D. Stucky, *Science*, 1998, 279, 548-552.
17 H. Essa, E. Magner, J. Cooney and B. K. Hodnett, *J. Mol. Catal. B-Enzym.*, 2007, 49, 61-68.
18 Y. Kawamura-Konishi, A. Asano, M. Yamazaki, H. Tashiro and H. Suzuki, *J. Mol. Catal. B-Enzym.*, 1998, 4, 181-190.

Example 3

Introduction:

Biocatalysis has long been of great interest for chemical, pharmaceutical, and food industries.[1] However, the successful utilization of proteins/enzymes as biocatalysts for applications in those aspects largely relies on the ability to successfully stabilize them in what is often an unnatural environment while retaining their functions and activities.[2] Immobilization of the biocatalysts on solid supports possesses the advantages of enhanced stability as well as ease separation and facile recovery for reuse.[3]

Over the past decade, porous metal-organic frameworks (MOFs) have emerged as a new type of functional materials.[4] That their nanospace can be decorated with functional organic groups for specific interactions with biomolecules, makes them attractive as host matrix materials to stabilize proteins/enzymes for biocatalysis applications. In particular, recent development of mesoporous MOFs may provide new opportunities for this content.[5]

Herein, we demonstrated that mesoporous MOFs could serve as a new type of platforms for biocatalysis, surpassing the mesoporous silica counterparts.[6,7]

Experimental Section

The biomolecules (MP-11 and Myoglobin) (FIG. 3.1a) were encapsulated into Tb-mesoMOF (FIG. 3.1b) under optimal conditions. The loading amount was quantified and the uptake profile is described by tracking the supernatant concentration of protein solution during incubation with Tb-mesoMOF. The immobilized catalysts are further characterized by BET test to confirm the change of the surface area and pore distribution, solid state UV-vis to probe the interaction between the cages and the enzyme guests and powder X-ray diffraction to verify the integrity of the MOF framework after catalysis.

To immobilize MP-11, freshly synthesized Tb-mesoMOF crystals were immersed in MP-11 solution of HEPES (4-(2-hydroxyethyl)-1-piperazineethanesulfonic acid) buffer, and placed in an incubator at 37° C. The uptake of MP-11 by Tb-mesoMOF was monitored by the disappearance of the Soret band at 400 nm in the supernatant.[8]

To explore the possibility to immobilize the large myoglobin (Mb) protein molecule, freshly prepared Tb-mesoMOF crystals were immersed in Mb solution of 4-(2-hydroxyethyl)-1-piperazineethanesulfonic acid (HEPES) buffer, and placed in an incubator at 37° C. The uptake of Mb by Tb-mesoMOF at different time points was determined by using the BCA method for protein determination.[9]

The catalytic performances of immobilized enzymes were investigated in many different reactions with various substates. MP-11@Tb-mesoMOF and Mb@Tb-mesoMOF have been investigated for different oxidation reactions under different conditions. Their performances were compared with the mesoporous silica counterparts, and the recyclability of these immobilized catalysts was also investigated.

Results and Discussion

A loading of 19.1 µmol/g was reached after ~50 hours for MP-11 immobilization into Tb-mesoMOF. As displayed in FIG. 3.2a, the color of Tb-mesoMOF crystals turns dark red after being saturated with MP-11. Single crystal optical absorption spectroscopy studies revealed that the spectra of MP-11@Tb-mesoMOF exhibit a Soret band at ~410 nm while the corresponding Soret band of MP-11 in buffer solution is 400 nm (FIG. 3.2b); the bathochromic shift of the encapsulated MP-11 in the Tb-mesoMOF is indicative of the interactions between the trapped MP-11 molecules and the hydrophobic nanoscopic cages.[10] $N_2$ sorption isotherms (FIG. 3.2c) measured at 77 K indicated that the BET surface area of Tb-mesoMOF decreases from 1935 $m^2$/g (Langmuir surface 3247 $m^2$/g) to 400 $m^2$/g (Langmuir surface 615 $m^2$/g) after saturation with MP-11, indicating a majority of the free space in Tb-mesoMOF is occupied by MP-11 molecules. Pore size distribution analysis revealed that the pore size of MP-11@Tb-mesoMOF is predominately around 0.9 nm while the pores of 4.1 nm and 3.0 nm observed in Tb-mesoMOF disappeared. We inferred from these observations that MP-11 molecules should reside in the nanoscopic cages after saturation, while the remaining micropores of 0.9 nm can provide an avenue for substrates to access the active MP-11 centers housed therein.

Free MP-11 in HEPES buffer solution demonstrates a fast initial rate of $8.93 \times 10^{-4}$ mM/sec (FIG. 3.3a; Table 1) as derived from the slope in the first two minutes. However, it starts to lose activity after only three minutes due to the aggregation in solution[11]. A initial rate of $7.58 \times 10^{-5}$ mM/sec (~30 min) and a final conversion of 48.7% is observed for MP-11@Tb-mesoMOF, which is much higher than the catalyst immobilized in the silica counterpart MCM-41 (Table 1).

TABLE 1

Summary of catalysis results of oxidizing DTBC to o-quinone in the presence of 10 mM $H_2O_2$ in methanol.

| | Free MP-11[a] | Tb-mesoMOF | MP-11@MCM-41 | MP-11@Tb-mesoMOF |
|---|---|---|---|---|
| Rate[b] (mM/sec) | $8.93 \times 10^{-4[c]}$ | $2.62 \times 10^{-6}$ | $3.57 \times 10^{-5}$ | $7.58 \times 10^{-5}$ |
| Conversion[d] (%) | 12.3 | 12.2 | 17.0 | 48.7 |

[a]Diluted to 0.6 μM in HEPES buffer;
[b]rate calculated from the first 30 minutes;
[c]Initial rate calculated in the first two minutes;
[d]final conversion after 25 hours.

The recyclability of MP-11@Tb-mesoMOF was also evaluated by checking its catalytic activities through seven cycles (FIG. 3.4).

The PXRD patterns indicated MP-11@Tb-mesoMOF can retain its MOF framework after the catalytic cycles (FIG. 3.5).

A saturated loading 7 of 9.1 μmol/g was reached after ~94 hours incubation of Myoglobin and Tb-mesoMOF (FIG. 3.6).

The color of Tb-mesoMOF crystal turns dark brown after being saturated with Mb as displayed in FIG. 3.7a. Solid-state UV-Vis absorption spectroscopy studies revealed that the spectra of Mb@Tb-mesoMOF exhibited a Soret band at ~410 nm consistent with the corresponding Soret band of Mb in buffer solution (FIG. 3.7b), indicating the integrity of the Mb protein molecule in Tb-mesoMOF. $N_2$ sorption isotherms (FIG. 3.7c) measured at 77 K indicated that the BET surface area of Tb-mesoMOF decreases from 1935 $m^2$/g (Langmuir surface 3247 $m^2$/g) to 462 $m^2$/g (Langmuir surface 642 $m^2$/g) after saturation with Mb. Pore size distribution analysis revealed that the pore size of Mb@Tb-mesoMOF is predominately around 0.8 nm while the pores of 4.1 nm and 3.0 nm observed in Tb-mesoMOF disappeared (FIG. 3.7d). We deduced from these observations that Mb molecules block the two types of mesopores, while the remaining micropores of 0.8 nm can provide a pathway for small substrates to access the active Mb centers housed in the 4.7 nm-diameter cages.

The peroxidase activity of Mb is usually assessed with the assay of 2,2'azinodi(3-ethylbenzthiazoline)-6-sulfonate (ABTS, molecular dimension 10.1 Å×17.3 Å) as a redox indicator by monitoring the rate of increase in absorbance at 660 nm ($\epsilon$=12 $mM^{-1}$ $cm^{-1}$ for ABTS+•) subsequent to the addition of peroxide (Scheme 1). To evaluate the biocatalytic activity as well as to confirm the possible size-selective biocatalysis performance of Mb@Tb-mesoMOF, we selected the small polyphenol 1,2,3-trihydroxybenzene (THB) which has a molecular dimension of 5.7 Å×5.8 Å as the substrate by monitoring its oxidation at 320 nm for the formation of the corresponding purpurogallin dimer product (molecular dimension: 5.8 Å×7.5 Å) (Scheme 2).

Scheme 1. Reaction scheme for oxidation of ABTS by hydrogen peroxide catalyzed by Mb.

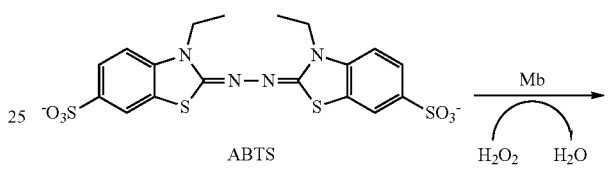

ABTS

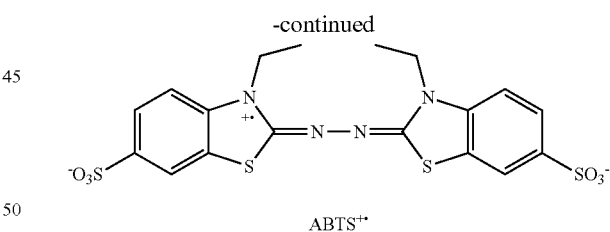

-continued

ABTS+•

Scheme 2. Reaction scheme for oxidation of THB by hydrogen peroxide catalyzed by Mb.

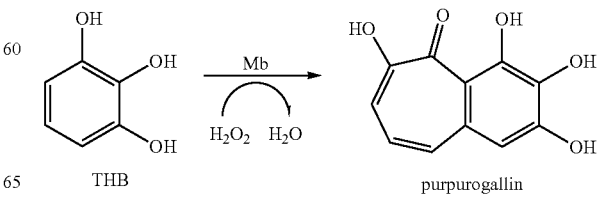

THB    purpurogallin

Given the small substrate molecule can access the active Mb centers through the 0.8 nm pore which can also facilitate the exit of the product molecule, we expected Mb@Tb-mesoMOF should exhibit a much higher activity of oxidizing THB compared to ABTS. As expected, Mb@Tb-mesoMOF demonstrates a high initial rate of $4.80 \times 10^{-5}$ mM/sec using THB as substrate (Table 2), which is about half of free Mb with a rate of $1.02 \times 10^{-4}$ mM/sec. The slower initial rate for Mb@Tb-mesoMOF compared to free Mb should originate from the slow diffusion of the substrates from solution into Mb@Tb-mesoMOF through the micropores of 0.8 nm. Whereas the observed high rate of $8.96 \times 10^{-5}$ mM/sec for Mb@SBA-15 can be attributed to the severe leaching of Mb, which actually was also responsible for the high initial rate for ABTS+• formation in Mb@SBA-15. Nevertheless, after one hour, Mb@Tb-mesoMOF exhibits a much faster average rate of $1.55 \times 10^{-5}$ mM/sec compared to Mb@SBA-15 (rate: $6.10 \times 10^{-6}$ mM/sec) and free Mb (rate: $8.20 \times 10^{-6}$ mM/sec). These results indicate that Mb@Tb-mesoMOF indeed demonstrates selective biocatalysis of oxidizing small THB over large ABTS due to the size effect, which to the best of our knowledge has never been reported before.

TABLE 2

Summary of catalysis results of oxidizing ABTS and THB in the presence of 10 mM $H_2O_2$ in HEPES buffer.

|  | Free Mb[a] | Mb@SBA-15 | Mb@Tb-mesoMOF |
|---|---|---|---|
| Initial rate for ABTS+• formation (mM/sec)[b] | $3.27 \times 10^{-4}$ | $2.00 \times 10^{-4}$ | $8.33 \times 10^{-6}$ |
| Initial rate for THB oxidation[c] (mM/sec) | $1.02 \times 10^{-5}$ | $8.96 \times 10^{-5}$ | $4.80 \times 10^{-5}$ |
| Average Rate for THB oxidation[d] (mM/sec) | $8.20 \times 10^{-6}$ | $6.10 \times 10^{-6}$ | $1.55 \times 10^{-5}$ |

[a]Diluted to 0.5 μM in HEPES buffer;
[b]initial rate calculated in the first four minutes;
[c]initial rate calculated in the first five minutes;
[d]average rate over one hour.

Conclusions

We have demonstrated for the first time the successful immobilization of MP-11 and Myoglobin into a mesoporous MOF consisting of nanoscopic cages, which demonstrate superior catalysis performances compared to mesoporous silica materials.

References, each of which is incorporated herein by reference
(1) Schmid, A.; Dordick, J. S.; Hauer, B.; Kiener, A.; Wubbolts, M.; Witholt, B. Nature 2001, 409, 258-268.
(2) S. Hudson, J. Cooney, E. Magner, Angew. Chem. 2008, 120, 8710-8723; Angew. Chem. Int. Ed. 2008, 47, 8582-8594.
(3) a) M. Hartmann, Chem. Mater. 2005, 17, 4577-4593; b) M. Hartmann, D. Jung, J. Mater. Chem. 2010, 20, 844-857.
(4) J. R. Long, O. M. Yaghi, Chem. Soc. Rev. 2009, 38, 1213-1214.
(5) Q.- R. Fang, T. A. Makal, M. D. Young, H.- C. Zhou, Comment Inorg. Chem, 2010, 31, 165-195.
(6) Lykourinou, V.; Chen, Y.; Wang, X.; Meng, L.; Hoang, T.; Ming, L.; Musselman, R. L.; Ma, S. J. Am. Chem. Soc. 2011, 133, 10382-10385.
(7) Chen, Y.; Lykourinou, V.; Wang, X.; Hoang, T.; Ming, L.; Ma, S. submitted.
(8) Nakamura, S.; Mashino, T.; Hirobe, M.; Tetrahedron Lett. 1992, 33, 5409-5412 (9) P. K. Smith, R. I. Krohn, G. T. Hermanson, F. H Gartner, E. K. Fujimoto, N. M. Goeke, B. J. Olson and D. C. Klenk, Anal. Biochem., 1985, 150, 76-85.
(10) Uchida, T.; Ishimori, K.; Morishima, I. J. Biol. Chem. 1997, 272, 30108-30114.
(11) Kadnikova, E. N.; Kostic, N. M. J. Org. Chem. 2003, 68, 2600-2608.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement technique and/or the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:
1. A composition comprising:
a mesoporous metal-organic framework (MOF) having at least one nanoscopic cage, wherein at least one nanoscopic cage includes a biomolecule, wherein the biomolecule is myoglobin or is selected from the group consisting of: microperoxidase, alcohol dehydrogenase, α-amylase, chloroperoxidase, α-chymotrypsin, glucose oxidase, horseradish peroxidase, laccase, lipase, manganese peroxidase, soybean peroxidase, trypsin, glycosylase, lysozyme, and a combination thereof, wherein the MOFs are coordination polymers with an inorganic-organic hybrid frame comprising metal ions or clusters of metal ions and organic ligands coordinated with the metal ions and/or clusters, wherein the MOFs are organized in a one-, two- or three-dimensional frameworks in which the metal clusters are linked to one another periodically by bridging ligands, pillar ligands, or a combination thereof, wherein the metal ions are selected from the group consisting of: Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, Bi, or di-metals thereof, wherein the metal ion has a 1+, 2+, 3+, 4+, 5+, 6+, 7+, or 8+ charge, wherein the bridging ligands and the pillar ligands include one or more functional groups that coordinate with the metal(s), link metal containing groups, or both, wherein the functional group is selected from the group consisting of $-CO_2H$, $-CS_2H$, $-NO_2$, $-B(OH)_2$, and $-SO_3H$, wherein the functional groups are bonded to the organic compound so to from the coordinative bond and of producing the framework material of the MOF, wherein the organic compound is selected from the group consisting of a polycarboxylated ligand, a polypyridyl ligand, a polycyano ligand, a polyphosphonate ligand, a polyhydroxyl ligand, a polysulfonate ligand, a polyimidazolate, ligand, a polytriazolate (both 1,2,3 and 1,2,4) ligand, polytetrazolate ligand, polypyrazolate ligand, and mixtures and combinations thereof.
2. The composition of claim 1, wherein the enzyme is microperoxidase.

3. The composition of claim 1, wherein the biomolecule is myoglobin.

4. The composition of claim 1, wherein the mesoporous MOF is a MOF with pore sizes larger than about 1.5 nm and cage diameters larger than about 2 nm.

5. The composition of claim 1, wherein the mesoporous MOF has a pore size of about 2 nm to 50 nm.

6. The composition of claim 1, wherein the mesoporous MOF is stable in water.

7. The composition of claim 1, wherein the nanoscopic cage of the mesoporous MOF has a diameter of about 3.9 to 4.7 nm.

8. The composition of claim 1, wherein the mesoporous MOF is loaded with the biomolecule in amount of about 1 to 1000 μmol/g.

9. A mesoporous metal-organic framework (MOF), comprising:
- at least one nanoscopic cage, wherein at least one nanoscopic cage includes a enzyme, wherein a nanoscopic cage has pore sizes larger than about 1.5 nm and a nanoscopic cage diameter larger than about 2 nm, and wherein the mesoporous MOF is stable in water, wherein the biomolecule is selected from the group consisting of:
- microperoxidase, alcohol dehydrogenase, α-amylase, chloroperoxidase, α-chymotrypsin, glucose oxidase, horseradish peroxidase, laccase, lipase, manganese peroxidase, soybean peroxidase, trypsin, glycosylase, lysozyme, and a combination thereof, wherein the MOFs are coordination polymers with an inorganic-organic hybrid frame comprising metal ions or clusters of metal ions and organic ligands coordinated with the metal ions and/or clusters, wherein the MOFs are organized in a one-, two- or three-dimensional frameworks in which the metal clusters are linked to one another periodically by bridging ligands, pillar ligands, or a combination thereof, wherein the metal ions are selected from the group consisting of: Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, Bi, or di-metals thereof, wherein the metal ion has a 1+, 2+, 3+, 4+, 5+, 6+, 7+, or 8+ charge, wherein the bridging ligands and the pillar ligands include one or more functional groups that coordinate with the metal(s), link metal containing groups, or both, wherein the functional group is selected from the group consisting of —$CO_2H$, —$CS_2H$, —$NO_2$, —$B(OH)_2$, and —$SO_3H$, wherein the functional groups are bonded to the organic compound so to from the coordinative bond and of producing the framework material of the MOF, wherein the organic compound is selected from the group consisting of a polycarboxylated ligand, a polypyridyl ligand, a polycyano ligand, a polyphosphonate ligand, a polyhydroxyl ligand, a polysulfonate ligand, a polyimidazolate, ligand, a polytriazolate (both 1,2,3 and 1,2,4) ligand, polytetrazolate ligand, polypyrazolate ligand, and mixtures and combinations thereof.

10. The MOF of claim 9, wherein the mesoporous MOF is loaded with the biomolecule in amount of about 1 to 1000 μmol/g.

11. The MOF of claim 9, wherein the enzyme is microperoxidase.

12. The MOF of claim 9, wherein the mesoporous MOF has a pore size of about 2 nm to 50 nm.

13. The MOF of claim 9, wherein the mesoporous MOF is stable in water.

14. The MOF of claim 9, wherein the nanoscopic cage of the mesoporous MOF has a diameter of about 3.9 to 4.7 nm.

\* \* \* \* \*